US012570617B2

(12) United States Patent
Bae et al.

(10) Patent No.: US 12,570,617 B2
(45) Date of Patent: Mar. 10, 2026

(54) USE OF TRIAZOLE COMPOUND AS GHRELIN RECEPTOR AGONIST

(71) Applicant: Kyungpook National University Industry-Academic Cooperation Foundation, Daegu (KR)

(72) Inventors: Jae Sung Bae, Daegu (KR); Hee Kyung Jin, Daegu (KR); Min Hee Park, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 442 days.

(21) Appl. No.: 18/027,829

(22) PCT Filed: Sep. 17, 2021

(86) PCT No.: PCT/KR2021/012823
§ 371 (c)(1),
(2) Date: Mar. 22, 2023

(87) PCT Pub. No.: WO2022/065831
PCT Pub. Date: Mar. 31, 2022

(65) Prior Publication Data

US 2023/0339869 A1 Oct. 26, 2023

(30) Foreign Application Priority Data

Sep. 22, 2020 (KR) ........................ 10-2020-0122540

(51) Int. Cl.

| | |
|---|---|
| ***C07D 255/02*** | (2006.01) |
| ***A61P 1/00*** | (2006.01) |
| ***A61P 3/02*** | (2006.01) |
| ***A61P 3/14*** | (2006.01) |
| ***A61P 21/00*** | (2006.01) |

(52) U.S. Cl.
CPC .............. *C07D 255/02* (2013.01); *A61P 1/00* (2018.01); *A61P 3/02* (2018.01); *A61P 3/14* (2018.01); *A61P 21/00* (2018.01)

(58) Field of Classification Search
CPC .. C07D 255/02; A61P 3/02; A61P 3/14; A61P 21/00; A61P 1/00
See application file for complete search history.

(56) References Cited

U.S. PATENT DOCUMENTS 8,334,256 B2 * 12/2012 Marsault .............. C07K 5/0812
514/4.8

FOREIGN PATENT DOCUMENTS

| | | | |
|---|---|---|---|
| KR | 20150020602 | A | 2/2015 |
| KR | 20170087813 | A | 7/2017 |
| KR | 20180110499 | A | 10/2018 |
| KR | 102017324 | B1 | 9/2019 |
| WO | 2011105611 | A1 | 9/2011 |
| WO | 2017075535 | A1 | 5/2017 |
| WO | 2019212196 | A1 | 11/2019 |

OTHER PUBLICATIONS

International Search Report in corresponding Korean Patent Application No. PCT/KR2021/012823, dated Dec. 23, 2021 (3 pages).
Yu Rong Guo, et al., "The Neuroprotective Effect of Amitriptyline on Radiation-Induced Impairment of Hippocampal Neurogenesis", An International Journal, pp. 1-8, Oct.-Dec. 2019.
Irina G. Bryndina, et al., "Clomipramine counteracts lipid raft disturbance due to short-term muscle disuse", Neuroscience Letters 664, pp. 1-6, 2018.
Jessica Bauer, et al., "Lipid Alterations in Experimental Murine Colitis: Role of Ceramide and Imipramine for Matrix Metalloproteinase-1 Expression", PLOSONE, pp. 1-8, Sep. 2009.
Karin Anne Becker, et al., "Sphingolipids as targets for inhalation treatment of cystic fibrosis", Advanced Drug Delivery Reviews 133, pp. 1-10, 2018.

* cited by examiner

*Primary Examiner* — Timothy R Rozof
(74) *Attorney, Agent, or Firm* — Carter, DeLuca & Farrell LLP; George Likourezos

(57) ABSTRACT

The present invention relates to a use of a triazole compound as a ghrelin receptor agonist and, more specifically, to a composition for preventing or treating diseases mediated by the ghrelin receptor, the composition being of a triazole compound which strongly binds to the ghrelin receptor with very high specificity. The compound provided by the present invention exhibits a strong binding force to the ghrelin receptor with very high specificity, and thus may be very usefully employed for preventing or developing a therapeutic agent for diseases mediated by the ghrelin receptor.

3 Claims, 18 Drawing Sheets

| | EC50 |
|---|---|
| Ghrelin | 39.45 nM |
| KARI001 | 128.3 nM |
| KARI101 | 188.5 nM |
| KARI201 | 272.9 nM |

USE OF TRIAZOLE COMPOUND AS GHRELIN RECEPTOR AGONIST

CROSS-REFERENCE TO RELATED APPLICATIONS

This is a National Stage Application filed under 35 U.S.C. 371 based on International Patent Application No. PCT/KR2021/012823, filed on Sep. 17, 2021, which claims priority to Korean Patent Application No. 10-2020-0122540, filed on Sep. 22, 2020, the disclosures of both of which are incorporated herein by reference in their entireties.

TECHNICAL FIELD

The present invention relates to a use of a triazole compound as a ghrelin receptor agonist and, more specifically, to a composition for preventing or treating diseases mediated by the ghrelin receptor, the composition being of a triazole compound which strongly binds to the ghrelin receptor with very high specificity.

BACKGROUND ART

Ghrelin is an endogenous ligand for growth hormone (GH) secretagogue receptors. Ghrelin, originally purified from the stomach, is a 28 amino acid peptide hormone in which the serine at position 3 is n-octanolized. Since it has a potential GH release action, ghrelin is considered to play an important role in maintaining GH release and energy homeostasis (see Non-patent reference 1). In particular, ghrelin seems to have a potential appetite-enhancing action. In addition, it is known for a ghrelin agonist to be useful for the treatment and/or prevention of cancer anorexia/cachexia (see Non-patent references 2, 3 and 4), cachexia and anorexia caused by anticancer drugs (see Non-patent references 4 and 5), hyperalgesia by anticancer drugs (see Non-patent reference 5), COPD/COPD cachexia (see Non-patent references 6 and 7), sarcopenia (see Non-patent reference 8), and eating disorders and neurogenic eating disorders (see Non-patent reference 9); inhibition of weight loss (see Non-patent reference 10); treatment and/or prevention of general weakness after surgery in cancer patients (see Non-patent reference 11), chronic airway infection (see Non-patent reference 7), inflammation (see Non-patent reference 12), IBD (see Non-patent reference 12), FD (see Non-patent reference 4), constipation (see Non-patent reference 9), diabetic gastroparesis and gastroparesis (see Non-patent references 4 and 13), heart failure (see Non-patent references 14, 15 and 16), myocardial infarction (see Non-patent references 14, 15 and 16), and diabetic neuropathy (see Non-patent reference 17); diagnosis and treatment of growth hormone deficiency (see Non-patent reference 18); improvement of the quality of life of the elderly (see Non-patent reference 18); and treatment and/or prevention of defecation disorders inpatients with spinal cord injury (see Non-patent reference 19), intestinal obstruction after surgery (see Non-patent references 4 and 20), anacidosis (see Non-patent reference 1) and morphine-induced intestinal obstruction (see Non-patent reference 20).

{Non-patent reference 1} Scientifica 2013, Article ID 518909 (http://dx.doi.org/10.1155/2013/518909), p. 25, 2013 {Non-patent reference 2} The Oncologist 12, pp. 594-600, 2007 {Non-patent reference 3} Support Care Cancer 21, pp. 2409-2415, 2013 {Non-patent reference 4} Neurogastroenterol Motil 20, 177-184, 2008 {Non-patent reference 5} Endocrinology 149, pp. 455-460, 2008 {Non-patent reference 6} BMC Pulmonary Medicine 13, pp. 37-46, 2013 {Non-patent reference 7} Methods in Enzymology 514, pp. 399-407, 2012 {Non-patent reference 8} Arch Med Sci 9, pp. 166-171, 2013 {Non-patent reference 9} Frontiers in Endocrinology 4, pp. 1-27, 2013 {Non-patent reference 10} Ann intern Med 149, pp. 601-611, 2008 {Non-patent reference 11} Gastric Cancer 17, pp. 200-205, 2014 {Non-patent reference 12} Mol Nutr Food Res 52, pp. 855-866, 2008 {Non-patent reference 13} Neurogastroenterol Motil 25, pp. e140-e150, 2013 {Non-patent reference 14} Journal of Cardiology 59, pp. 8-13, 2012 {Non-patent reference 15} Curr Opin Clin Nutr Metab Care 16, pp. 619-624, 2013 {Non-patent reference 16} Endocrinology 153, pp. 2436-2443, 2012 {Non-patent reference 17} Biochemical and Biophysical Research Communications 389, pp. 405-408, 2009 {Non-patent reference 18} Drug Discovery Today 4, pp. 497-506, 1999 {Non-patent reference 19} Neurogastroenterol Motil 21, pp. 71-77, 2009 {Non-patent reference 20} Peptides 26, pp. 1598-1601, 2005, {Patent reference 1} KR 2014-7036310 A Therefore, it is desirable to find new compounds that modulate ghrelin receptor action.

SUMMARY OF INVENTION

Technical Problem

As a result of intensive research to develop a ghrelin receptor agonist which binds to a ghrelin receptor with very high specificity, the inventors of the present invention found that triazole-based compounds exhibit such efficacy, and have completed the present invention.

Accordingly, an object of the present invention is to provide a pharmaceutical composition for preventing or treating diseases mediated by a ghrelin receptor, comprising a compound of the following Formula 1 or a pharmaceutically acceptable salt thereof as an active ingredient.

In addition, an object of the present invention is to provide a pharmaceutical composition for preventing or treating diseases mediated by a ghrelin receptor, consisting of a compound of the following Formula 1 or a pharmaceutically acceptable salt thereof.

In addition, an object of the present invention is to provide a pharmaceutical composition for preventing or treating diseases mediated by a ghrelin receptor, consisting essentially of a compound of the following Formula 1 or a pharmaceutically acceptable salt thereof:

[Formula 1]

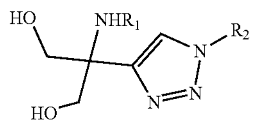

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

Another object of the present invention is to provide a food composition for preventing or improving diseases mediated by a ghrelin receptor, comprising a compound of the following Formula 1 or a pharmaceutically acceptable salt thereof as an active ingredient.

Another object of the present invention is to provide a food composition for preventing or improving diseases mediated by a ghrelin receptor, consisting of a compound of the following Formula 1 or a pharmaceutically acceptable salt thereof.

In addition, another object of the present invention is to provide a food composition for preventing or improving diseases mediated by a ghrelin receptor, consisting essentially of a compound of the following Formula 1 or a pharmaceutically acceptable salt thereof:

[Formula 1]

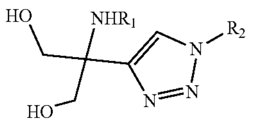

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

Another object of the present invention is to provide a compound of the following Formula 2 or a salt thereof:

[Formula 2]

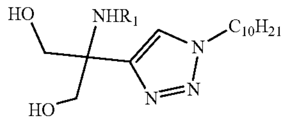

wherein $R_1$ is hydrogen; straight or branched chain alkyl having 1 to 15 carbon atoms; or a substituted or unsubstituted alkylcarbonyl having 1 to 5 carbon atoms.

Another object of the present invention is to provide a use of a compound of the above-identified Formula 1 or a pharmaceutically acceptable salt thereof in preparing an agent for the treatment of diseases mediated by a ghrelin receptor.

Another object of the present invention is to provide a method for treating diseases mediated by a ghrelin receptor, comprising administering an effective amount of a composition comprising a compound of the above-identified Formula 1 or a pharmaceutically acceptable salt thereof to a subject in need thereof.

Solution to Problem

In order to achieve the above-identified object of the present invention, the present invention provides a pharmaceutical composition for preventing or treating diseases mediated by a ghrelin receptor, comprising a compound of the following Formula 1 or a pharmaceutically acceptable salt thereof as an active ingredient.

In addition, the present invention provides a pharmaceutical composition for preventing or treating diseases mediated by a ghrelin receptor, consisting of a compound of the following Formula 1 or a pharmaceutically acceptable salt thereof.

In addition, the present invention provides a pharmaceutical composition for preventing or treating diseases mediated by a ghrelin receptor, consisting essentially of a compound of the following Formula 1 or a pharmaceutically acceptable salt thereof:

[Formula 1]

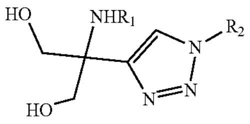

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

In order to achieve another object of the present invention, the present invention provides a food composition for preventing or improving diseases mediated by a ghrelin receptor, comprising a compound of the following Formula 1 or a pharmaceutically acceptable salt thereof as an active ingredient.

In addition, the present invention provides a food composition for preventing or improving diseases mediated by a ghrelin receptor, consisting of a compound of the following Formula 1 or a pharmaceutically acceptable salt thereof as an active ingredient.

In addition, the present invention provides a food composition for preventing or improving diseases mediated by a ghrelin receptor, consisting essentially of a compound of the following Formula 1 or a pharmaceutically acceptable salt thereof as an active ingredient:

[Formula 1]

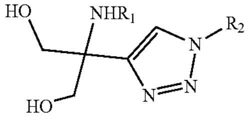

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

In order to achieve another object of the present invention, the present invention provides a compound of the following Formula 2 or a salt thereof:

[Formula 2]

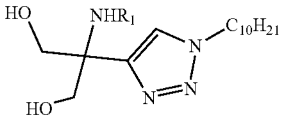

wherein $R_1$ is hydrogen; straight or branched chain alkyl having 1 to 15 carbon atoms; or a substituted or unsubstituted alkylcarbonyl having 1 to 5 carbon atoms.

In order to achieve another object of the present invention, the present invention provides a use of a compound of the above-identified Formula 1 or a pharmaceutically acceptable salt thereof in preparing an agent for the treatment of diseases mediated by a ghrelin receptor.

In order to achieve another object of the present invention, the present invention provides a method for treating diseases mediated by a ghrelin receptor, comprising administering an effective amount of a composition comprising a compound of the above-identified Formula 1 or a pharmaceutically acceptable salt thereof to a subject in need thereof.

Hereinafter, the present invention will be described in detail.

The present invention provides a pharmaceutical composition for preventing or treating diseases mediated by a ghrelin receptor, comprising a compound of the following Formula 1 or a pharmaceutically acceptable salt thereof as an active ingredient:

[Formula 1]

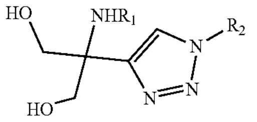

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

In the present invention, the "alkyl" refers to straight or branched chain hydrocarbon having 1 to 15 carbon atoms. Representative examples of alkyl comprise methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, undecyl and dodecyl, but the present invention is not limited thereto.

As used herein, the term "carbonyl" refers to a —C(O)— group.

In the present invention, the "alkylcarbonyl" refers to the alkyl group attached to the parent molecular moiety through a carbonyl group as defined above. Representative examples of alkylcarbonyl comprise acetyl, 1-oxopropyl, 2,2-dimethyl-1-oxopropyl, 1-oxobutyl and 1-oxopentyl, but the present invention is not limited thereto.

In the present invention, when the alkylcarbonyl is "substituted" alkylcarbonyl, it may be substituted with one or more substituents selected from the group consisting of hydroxy, halogen, cyano, nitro and amino.

In the present invention, the "alkenyl" refers to straight-chain or branched-chain hydrocarbon having 2 to 10 carbon atoms containing at least one carbon-carbon double bond formed by the removal of two hydrogen atoms. Representative examples of alkenyl comprise ethenyl, 2-propenyl, 2-methyl-2-propenyl, 3-butenyl, 4-pentenyl, 5-hexenyl, 2-heptenyl, 2-methyl-1-heptenyl and 3-decenyl, but the present invention is not limited thereto.

In the present invention, the "alkynyl" refers to a straight or branched chain hydrocarbon group having 2 to 10 carbon atoms comprising at least one carbon-carbon triple bond. Representative examples of alkynyl comprise acetylenyl, 1-propynyl, 2-propynyl, 3-butynyl, 2-pentynyl and 1-butynyl, but the present invention is not limited thereto.

Preferably, in the present invention, $R_1$ may be hydrogen or acetyl, and $R_2$ may be alkyl having 1 to 15 carbon atoms. More preferably, in the present invention, $R_1$ may be hydrogen, and $R_2$ may be alkyl having 4 to 15 carbon atoms. Even more preferably, in the present invention, $R_1$ may be hydrogen, and $R_2$ may be alkyl having 6 to 12 carbon atoms. Most preferably, in the present invention, $R_1$ may be hydrogen, and $R_2$ may be alkyl having 9 to 12 carbon atoms.

Specifically, in the present invention, a compound of the above-identified compound Formula 1 may be 2-amino-2-(1-hexyl-1H-1,2,3-triazol-4-yl)propan-1,3-diol, 2-amino-2-(1-heptyl-1H-1,2,3-triazol-4-yl)propane-1,3-diol, 2-amino-2-(1-octyl-1H-1,2,3-triazol-4-yl)propane-1,3-diol, 2-amino-2-(1-nonyl-1H-1,2,3-triazol-4-yl)propan-1,3-diol, 2-amino-2-(1-decyl-1H-1,2,3-triazol-4-yl)propane-1,3-diol, 2-amino-2-(1-undecyl-1H-1,2,3-triazol-4-yl)propane-1,3-diol or 2-amino-2-(1-dodecyl-1H-1,2,3-triazol-4-yl)propane-1,3-diol.

According to one embodiment of the present invention, it was confirmed that a compound of the above-identified Formula 1 exhibits a very strong binding force to a ghrelin receptor and has very high binding specificity to the ghrelin receptor. Therefore, it may be expected that the compound of the above-identified Formula 1 exhibits an effect of preventing or treating diseases mediated by a ghrelin receptor as a ghrelin receptor agonist and does not affect the activities of other receptors to show low side effects.

The action of the endogenous ligand ghrelin in the ghrelin receptor has been shown to lead to potential growth hormone release, appetite stimulation, gastric motility, acid secretion, positive cardiovascular effects and direct bone formation. Therefore, ghrelin receptor agonists may achieve good effects in the treatment of growth hormone deficiency, eating disorders, gastrointestinal diseases, cardiovascular diseases, osteoporosis, aging and catabolic or chronic wasting syndrome. Ghrelin receptor agonists may also have beneficial effects in the treatment of sleep disorders.

Certain diseases associated with a ghrelin receptor and therefore mediated by a ghrelin receptor and for which ghrelin receptor agonists may benefit comprise obesity and obesity-related risk factors. In addition, obesity-related risk factors comprise diabetes, diabetes-related complications, metabolic syndrome and cardiovascular abnormalities (e.g., atherosclerosis and dyslipidemia), but the present invention is not limited thereto.

Other diseases and/or conditions mediated by a ghrelin receptor comprise: treating growth hormone deficiency conditions, increasing muscle mass, increasing bone density, treating male and female sexual dysfunction, facilitating weight gain, facilitating weight maintenance, facilitating appetite (For example, facilitating weight gain, weight maintenance, or appetite enhancement is useful for patients with disorders associated with weight loss or undergoing the treatment). Examples of diseases or conditions accompanying weight loss comprise anorexia, bulimia, cancer cachexia, AIDS, wasting disease, cachexia, and wasting in the frail elderly. Examples of treatments accompanying weight loss comprise chemotherapy, radiotherapy, temporary or permanent immobilization and dialysis.

Other diseases or conditions comprise improving sleep disorders, congestive heart failure, metabolic disorders, memory function reduction, breast cancer, thyroid cancer, ischemic nerve or muscle damage.

Eating disorders comprise anorexia which comprises subtypes of restrictive, binge eating and elimination; bulimia which comprises subtypes of elimination and non-elimination; obesity; compulsive eating disorder; binge eating disorder; and other unspecified eating disorders.

Gastrointestinal conditions for which ghrelin receptor agonists may be effective comprise gastric obstruction, gastric ulcers, inflammatory bowel diseases such as Crohn's disease, and ulcerative colitis. The compounds of the present invention are useful for the treatment of alleviating symptoms associated with esophageal reflux and/or dyspepsia that accompany or do not accompany appetite/metabolic cachexia, and for the treatment of symptoms associated with constipation such as paralytic ileus or pseudoobstruction and constipation preferential irritable bowel syndrome.

The cardiovascular diseases comprise heart failure and dilated cardiomyopathy.

A catabolic state or chronic wasting syndrome may occur in postoperative patients and also comprises AIDS-related wasting syndromes and cancer-related wasting syndromes such as cancer cachexia.

Ghrelin receptor agonists are known to promote gastric acid secretion (see KR 2014-7036310 A). Therefore, the effect of enhancing gastric acid secretion suggests that the ghrelin receptor agonist of the present invention may be effective in treating various diseases accompanied by low or no gastric acid secretion.

In the present invention, anacidosis is not particularly limited to some types and may comprise age-related anacidosis accompanying the aging process; chronic gastritis-related anacidosis; anemic anoxia with anemic symptoms; partial gastrectomy-related anoxia; calcium absorption-related anacemia; vitamin D absorption-related anacidosis; calcitonin synthesis-related anoxia; and drug-induced anoxia.

In one aspect of the present invention, a compound of the above-identified compound Formula 1 may exhibit an effect of preventing or treating ghrelin receptor-diseases selected from the group consisting of cancer anorexia or cachexia; cachexia or anorexia due to anticancer drugs; hyperalgesia due to anticancer drugs; COPD or COPD cachexia; sarcopenia; eating disorders; weight loss; generalized weakness after surgery in cancer patients; chronic airway infection; inflammation; IBD; FD; constipation; diabetic gastroparesis; heart failure; myocardial infarction; diabetic neuropathy; growth hormone deficiency; defecation disorders in patients with spinal injuries; postoperative ileus; anoxia; and morphine-induced intestinal obstruction.

In the present invention, examples of the pharmaceutically acceptable salt comprise an acid addition salt formed from inorganic acids (e.g., hydrochloric acid, hydrobromic acid, sulfuric acid, phosphoric acid and nitric acid), and a salt formed from organic acids (e.g., acetic acid, oxalic acid, tartari acid, succinic acid, malic acid, fumaric acid acid, maleic acid, ascorbic acid, benzoic acid, tannic acid, pamoic acid, alginic acid, polyglutamic acid, naphthalene sulfonic acid, naphthalene disulfonic acid and poly-galacturonic acid). The compound may also be administered in the form of a pharmaceutically acceptable quaternary salt known to those skilled in the art, which, in particular, comprises chloride, bromide, iodide, —O-alkyl, toluenesulfonate, methylsulfonate, sulfonate, phosphate or carboxylate (e.g., benzoates, succinates, acetates, glycolate, maleate, malate, fumarate, citrate, tartrate, ascorbates, cinnamoate, mandeloate and diphenylacetate), but the present invention is not limited thereto.

The pharmaceutical composition according to the present invention may be Formulated in a suitable form together with a pharmaceutically acceptable carrier and additionally comprise an excipient or a diluent. In the above, 'pharmaceutically acceptable' refers to a non-toxic composition that is physiologically acceptable and does not cause an allergic reaction such as gastrointestinal disorder and dizziness, or a reaction similar thereto when administered to a human being.

A pharmaceutically acceptable carrier may further comprise, for example, a carrier for oral administration or a carrier for parenteral administration. A carrier for oral administration may comprise lactose, starch, cellulose derivatives, magnesium stearate and stearic acid. In addition, the carrier for parenteral administration may comprise water, suitable oil, saline, aqueous glucose and glycol, and additionally comprise a stabilizer and a preservative. Suitable stabilizers comprise antioxidants such as sodium bisulfite, sodium sulfite and ascorbic acid. Suitable preservatives comprise benzalkonium chloride, methyl- or propylparaben and chlorobutanol. The pharmaceutical composition of the present invention may further comprise a lubricant, a wetting agent, a sweetening agent, a flavoring agent, an emulsifier and a suspending agent in addition to the above-identified components. Other pharmaceutically acceptable carriers and agents may be referred to those known in the art.

The composition of the present invention may be administered to mammals comprising human beings by any method. For example, it may be administered orally or parenterally. Parenteral administration methods comprise intravenous, intramuscular, intraarterial, intramedullary, intrathecal, intracardiac, transdermal, subcutaneous, intraperitoneal, intranasal, intestinal, topical, sublingual or rectal administration, but the present invention is not limited thereto.

The pharmaceutical composition of the present invention may be Formulated into a Formulation for oral administration or parenteral administration according to the administration route as described above.

In the case of a Formulation for oral administration, the composition of the present invention may be Formulated into powders, granules, tablets, pills, dragees, capsules, solutions, gels, syrups, slurries, suspensions, etc. by using methods known in the art. For example, as a Formulation for oral administration, tablets or dragees may be obtained by mixing an active ingredient with a solid excipient, milling the mixture, adding suitable auxiliaries thereto and processing the mixture into a mixture of granules. Examples of suitable excipients comprise sugars (e.g., lactose, dextrose, sucrose, sorbitol, mannitol, xylitol, erythritol and maltitol), starches (e.g., corn starch, wheat starch, rice starch and potato starch), celluloses (e.g., cellulose, methylcellulose, sodium carboxymethylcellulose and hydroxypropylmethylcellulose), and fillers such as gelatin and polyvinylpyrrolidone. In addition, cross-linked polyvinylpyrrolidone, agar, alginic acid or sodium alginate may be added as a disintegrant. Furthermore, the pharmaceutical composition of the present invention may further comprise an anticoagulant, a lubricant, a wetting agent, a flavoring agent, an emulsifier and a preservative.

In the case of a Formulation for parenteral administration, it may be Formulated in the form of injections, creams, lotions, external ointments, oils, moisturizers, gels, aerosols and nasal inhalants by methods known in the art. These Formulations are described in prescriptions generally known in all pharmaceutical chemistry fields.

The total effective amount of the composition of the present invention may be administered to a patient in a single dose or by a fractionated treatment protocol of administering a composition in multiple doses over a long period of time. The amount of the active ingredient contained in the pharmaceutical composition of the present invention may vary according to the severity of the disease. The total dose of the pharmaceutical composition of the present invention may be preferably about 0.01 μg to 10,000 mg, most preferably 0.1 μg to 1000 mg per kg of patient body weight per day. However, the dose of the pharmaceutical composition is determined by considering a Formulation method, an administration route and the number of treatments and other various factors (e.g., a patient's age, weight, health condition, sex, severity of disease, diet and excretion rate). Therefore, considering this point, those skilled in the art will be able to determine an appropriate effective dose of the composition of the present invention. As long as the pharmaceutical composition according to the present invention exhibits the effects of the present invention, its Formulation, administration route and administration method are not particularly limited.

The present invention also provides a food composition for preventing or improving diseases mediated by a ghrelin receptor, comprising a compound of the following Formula 1 or a pharmaceutically acceptable salt thereof as an active ingredient:

[Formula 1]

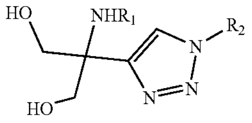

wherein $R_1$ is hydrogen; straight or branched chain alkyl having 1 to 15 carbon atoms; or substituted or unsubstituted alkylcarbonyl having 1 to 5 carbon atoms, and $R_2$ is hydrogen; straight or branched chain alkyl having 1 to 15 carbon atoms; alkenyl having 2 to 10 carbon atoms; or alkynyl having 2 to 10 carbon atoms.

The food composition according to the present invention comprises all types of functional foods, nutritional supplements, health foods and food additives. The above-identified types may be produced in various forms according to methods conventionally known in the art.

For example, as a health food, the food composition of the present invention may be produced in the form of tea, juice or drink to be consumed, or granulated, encapsulated or powdered to be consumed. In addition, the food composition of the present invention may be produced in the form of a composition by mixing with a substance or an active ingredient known to have an effect of preventing, improving or treating neurodegenerative diseases or depression.

In addition, functional foods may be produced by adding the food composition of the present invention to beverages (e.g., alcoholic beverages), fruits and their processed foods (e.g., canned fruit, bottled fruit, jam and marmalade), fish, meat, and their processed foods (e.g., ham and sausage corn beef), breads and noodles (e.g., udon, buckwheat noodles, ramen, spaghetti and macaroni), fruit juice, various drinks, cookies, taffy, dairy products (e.g., butter and cheese), edible vegetable oil, margarine, vegetable protein, retort food, frozen food, various seasonings (e.g., soybean paste, soy sauce and sauce).

The amount of the food composition according to the present invention is preferably 0.01 to 50% by weight based on the total weight of the final food product, but the present invention is not limited thereto. In order to use the food composition of the present invention in the form of a food additive, it may be produced and used in the form of a powder or a concentrate.

The present invention also provides a compound of the following Formula 2 or a salt thereof:

[Formula 2]

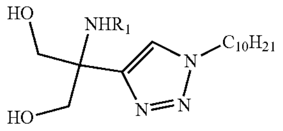

wherein $R_1$ is hydrogen; straight or branched chain alkyl having 1 to 15 carbon atoms; or a substituted or unsubstituted alkylcarbonyl having 1 to 5 carbon atoms.

In the above-identified Formula, alkyl and alkylcarbonyl may be applied in the same manner as described above.

Preferably, $R_1$ is hydrogen or acetyl.

Most preferably, the compound of Formula 2 may be 2-amino-2-(1-decyl-1H-1,2,3-triazol-4-yl)propane-1,3-diol.

The compound of Formula 2 provided by the present invention is characterized in that it acts as a ghrelin receptor-specific agonist and may be used as a preventive or therapeutic agent for diseases mediated by a ghrelin receptor.

In one aspect of the present invention, the compound of Formula 2 provided by the present invention comprises a salt form thereof, and the salt may preferably be in the form of a pharmaceutically acceptable salt form.

Examples of such salt comprise an acid addition salt formed from inorganic acids (e.g., hydrochloric acid, hydrobromic acid, sulfuric acid, phosphoric acid and nitric acid], and a salt formed from organic acids (e.g., acetic acid, oxalic acid, tartari acid, succinic acid, malic acid, fumaric acid, maleic acid acid, ascorbic acid, benzoic acid, tannic acid, pamoic acid, alginic acid, polyglutamic acid, naphthalene sulfonic acid, naphthalene disulfonic acid and polygalacturonic acid), but the present invention is not limited thereto. The compound may also be administered in the form of a pharmaceutically acceptable quaternary salt known to those skilled in the art, which, in particular, comprises chloride, bromide, iodide, —O-alkyl, toluenesulfonate, methylsulfonate, sulfonate, phosphate, or carboxylate (e.g., benzoate, succinate, acetate, glycolate, maleate, malate, fumarate, citrate, tartrate, ascorbate, cinnamoate, mandeloate and diphenylacetate).

In order to achieve another object of the present invention, the present invention provides a use of the compound of Formula 1 or a pharmaceutically acceptable salt thereof in preparing an agent for the treatment of diseases mediated by a ghrelin receptor.

In order to achieve another object of the present invention, the present invention provides a method for treating diseases mediated by a ghrelin receptor, comprising administering an effective amount of a composition comprising the compound of Formula 1 or a pharmaceutically acceptable salt thereof to a subject in need thereof.

The 'effective amount' of the present invention refers to an amount that exhibits an effect of improving, treating, preventing, detecting, diagnosing, or suppressing or reducing diseases mediated by a ghrelin receptor when administered to a subject, and the 'subject' refers to an animal, preferably a mammal, especially an animal comprising a human being, and may also be a cell, a tissue, an organ or others derived from an animal. The subject may be a patient in need of the effect.

The ‘treatment’ of the present invention comprehensively refers to improving diseases mediated by a ghrelin receptor or symptoms of the diseases, which may comprise curing, substantially preventing or improving the conditions of the diseases, or alleviating, curing or preventing one or most of the symptoms resulting from the diseases, but the present invention is not limited thereto.

In the specification of the present invention, the term “comprising” is used in the same meaning as “including” or “characterized by,” and the composition or method according to the present invention does not exclude additional components or steps of the method not specifically mentioned. In addition, the term “consisting of” refers to excluding additional elements, steps or components not specifically described. The term “essentially consisting of” means that the composition or method comprises described materials or steps and may comprise materials or steps that do not substantially affect the basic characteristics thereof.

Advantageous Effects of Invention

The compound provided by the present invention shows a strong binding force with very high specificity to a ghrelin receptor and, thus, may be very useful for the development of preventive or therapeutic agents for diseases mediated by a ghrelin receptor.

MODE FOR INVENTION

Figure 1:
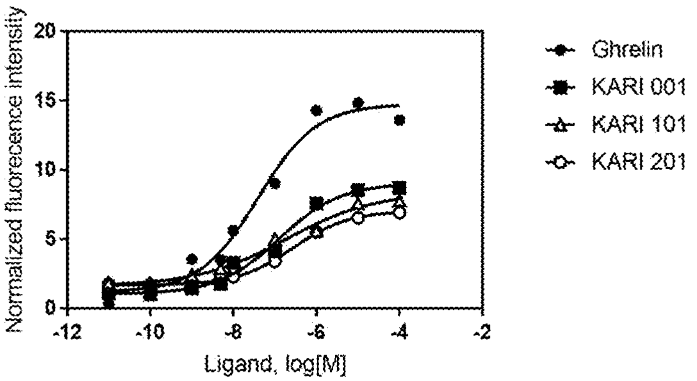
FIG. 1 is a diagram showing EC50 that may represent 50% intracellular calcium influx according to concentrations of ghrelin and triazole compounds (KARI001, KARI101 and KARI201) in human embryonic kidney 293 (HEK293) cells overexpressing a ghrelin receptor.

Hereinafter, the present invention will be described in detail by the following embodiments. However, the following embodiments are only for illustrating the present invention, and the present invention is not limited thereto.

<Test Materials and Test Methods>

0. Synthesis of Compounds

Substances KARI001 and KARI201 were produced and synthesized in view of an existing reference (Korean Patent No. 2017324). A ghrelin protein used as a positive control was purchased from TORIS.

KARI001:
2-amino-2-(1-dodecyl-1H-1,2,3-triazol-4-yl)propane-1,3-diol

KARI201:
2-amino-2-(1-nonyl-1H-1,2,3-triazol-4-yl)propane-1,3-diol

Substance KARI101, compound 2-amino-2-(1-decyl-1H-1,2,3-triazol-4-yl) propane-1,3-diol, was produced through the following series of processes.

0-1. Scheme 1: Synthesis of 1-azidodecane

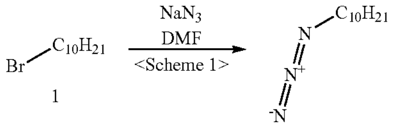

1 2

To synthesize 1-azidodecane of Scheme 1, sodium azide (4.9 g, 75 mmol, 2 eq) was added to a solution of 1-bromodecane (9.9 g, 37 mmole) of Formula 1 in DMF (50 ml). The mixture was stirred at room temperature for 2 days and ice water (200 ml) was added thereto to extract with ether.

The organic layer was dried over $H_2O$, brine and $MgSO_4$ and concentrated to obtain 1-azidodecane of Formula 2 (6.2 g, 91%).

$^1H$ NMR (400 MHz, $CDCl_3$): δ 3.28 (t, 2H), 1.62 (m, 2H,), 1.40-1.29 (m, 14H), 0.91 (t, 3H)

0-2. Scheme 2: Synthesis of 2-amino-2-(hydroxymethyl)propane-1,3-diol

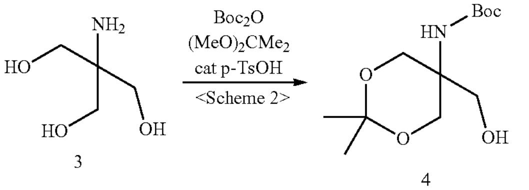

3 4

To synthesize 2-amino-2-(hydroxymethyl)propane-1,3-diol of Scheme 2, $Boc_2O$ (49.5 g, 1.1 eq) was added to the suspension of tris(hydroxymethyl)amino-methane of Formula 3 (25.0 g, 0.206 mol) in DMF (500 ml). After the mixture was stirred at room temperature for 2 hours, 2,2-dimethoxypropane (30.4 ml, 1.2 eq) and p-TsOH·$H_2O$ (2.0 g, 0.05 eq) were added thereto. The mixture was stirred at room temperature for 18 hours and diluted with $Et_2O$ (500 ml). The organic layer was washed with saturated $NaHCO_3$ solution (300 ml) and brine (200 ml). The organic layer was dried over $MgSO_4$ and concentrated. The residue was crystallized with n-hexane to obtain tert-butyl 5-(hydroxymethyl)-2,2-dimethyl-1,3-dioxan-5-ylcarbamate of Formula 4 as a white solid (32.0 g, 59.4%).

$^1H$ NMR (600 MHz, $CDCl_3$): δ 5.32 (s, 1H), 3.86-3.80 (m, 4H), 3.73 (s, 2H), 3.68 (s, 1H), 1.46-1.44 (m, 15H)

0-3. Scheme 3: Synthesis of 2-amino-2-(hydroxymethyl)propane-1,3-diol

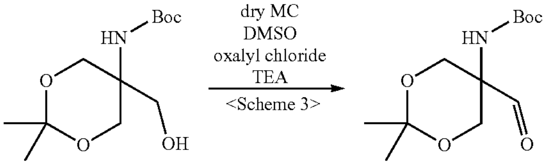

4 5

To synthesize tert-butyl 5-formyl-2,2-dimethyl-1,3-dioxan-5-ylcarbamate of Scheme 3, a solution of oxalyl chloride (33.4 ml, 3.17 eq) in dried MC (340 ml) was mixed with DMSO (43.7 ml, 5 eq). The mixture was stirred for 15 minutes and then mixed with tert-butyl 5-(hydroxymethyl)-2,2-dimethyl-1,3-dioxan-5-ylcarbamate of Formula 4 (32.0 g, 0.123 mol) in anhydrous MC (340 ml). After the mixture was stirred for 2 hours, $Et_3N$ (171 ml, 10 eq) was added thereto. The mixture was stirred for 10 minutes, the cooling bath was then removed, and the mixture was left at room temperature. The light brown suspension was diluted with EA (300 ml) and washed with 10% $NH_4OH$ (1, 500 ml). The organic layer was concentrated and applied to $SiO_2$ column chromatography eluting the residue by EA/n-hexane=1/10 to obtain tert-butyl 5-formyl-2,2-dimethyl-1,3-dioxane-5-ylcarbamate of Formula 5 (15.0 g, 47.2%) as a white solid.

$^1H$ NMR (400 MHz, $C_DCl3$): δ 9.64 (s, 1H), 5.56 (s, 1H), 4.07 (d, 2H, J=12.0 Hz), 3.95 (d, 2H, J=12.0 Hz), 1.47 (s, 15H)

0-4. Scheme 4: Synthesis of 2-amino-2-(hydroxymethyl)propane-1,3-diol

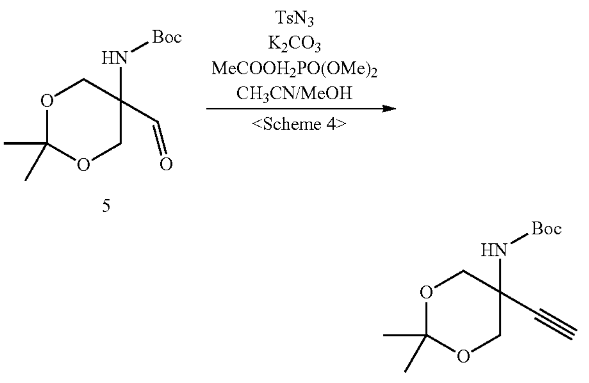

5 6

To synthesize tert-butyl 5-ethynyl-2,2-dimethyl-1,3-dioxan-5-ylcarbamate of Scheme 4, dimethyl-2-oxopropylphosphonate (1.6 g, 1.02 eq) was added to an acetonitrile (50 ml) suspension comprising $K_2CO_3$ (3.0 g, 2.25 eq) and p-toluenesulfonylazide (14% solution in toluene, 15.8 ml, 1.05 eq), and the mixture was vigorously stirred at room temperature for 2.5 hours. A solution of tert-butyl 5-formyl-2,2-dimethyl-1,3-dioxan-5-ylcarbamate of Formula 5 (2.5 g, 9.64 mmol) contained in methanol (40 ml) was added to the first reaction mixture. After adding $K_2CO_3$ (2.7 g, 2.06 eq), the mixture was stirred for 1.5 hours and concentrated under a reduced pressure, and the residue was diluted with MC (200 ml) and $H_2O$ (200 ml). The organic layer was washed with $H_2O$ (200 ml), dried over $MgSO_4$ and concentrated under a reduced pressure. The residue was eluted by EA/n-hexane=1/9 and applied to $SiO_2$ column chromatography to obtain tert-butyl 5-ethynyl-2,2-dimethyl-1,3-dioxan-5-ylcarbarmate of Formula 6 (2.3 g, 93.4%) as a white solid.

$^1H$ NMR (400 MHz, $C_DCl3$): δ 5.15 (s, 1H), 4.05-3.95 (m, 4H), 2.43 (s, 1H), 1.48-1.38 (m, 15H)

0-5. Scheme 5: Synthesis of 2-amino-2-(1-decyl-1H-1,2,3-triazol-4-yl)propane-1,3-diol hydrochloride

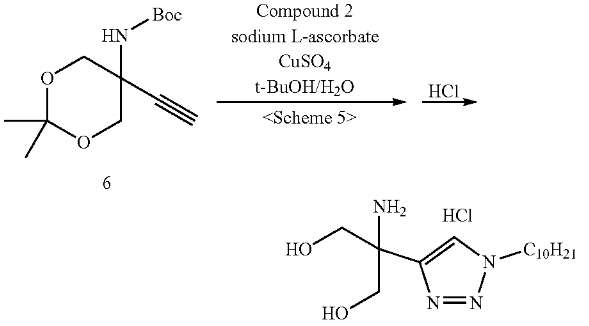

6

KARI 101

To synthesize 2-amino-2-(1-decyl-1H-1,2,3-triazol-4-yl) propane-1,3-diol, which is KARI101 of Scheme 5, $CuSO_4 \cdot 5H_2O$ (1.56 g, 6 mmol) was added to a solution of tert-butyl 5-ethynyl-2,2-dimethyl-1,3-dioxan-5-ylcarbamate (4.0 g, 15 mmol), 1-azidodecane of Scheme 1 (3.16 g, 17 mmol), sodium L (4.03 g, 20 mmol), t-BuOH (60 ml), $H_2O$ (128 ml) and MC (104 ml). The two-phase solution was stirred in air for 18 hours, and the aqueous layer was extracted with MC. The organic layer was dried over $MgSO_4$ and concentrated under a reduced pressure. The residue was eluted by EA/n-hexane=1/6 and applied to $SiO_2$ column chromatography to obtain a solid (6.5 g). The resulting solid was mixed with concentrated HCL (21 ml) and ethanol (210 ml) and stirred at room temperature for 6 hours. The reaction mixture was concentrated under a reduced pressure and recrystallized from acetone to obtain 2-amino-2-(1-decyl-1H-1,2,3-triazol-4-yl)propane-1,3-diol as a white solid (2.6 g, 52.4%, molecular weight 298.4).

$^1H$ NMR (500 MHz, methanol-$d_4$): δ 8.06 (s, 1H), 4.41 (t, 2H), 3.95 (dd, J=20 Hz, 15 Hz, 4H), 1.91 (t, 2H), 1.29-1.33 (m, 14H), 0.89 (t, 3H)

$^{13}C$ NMR (500 MHz, methanol-$d_4$): δ 144.9, 124.3, 63.7 (2C), 60.8, 51.5, 33.0, 31.3, 30.6, 30.5, 30.4, 30.1, 27.5, 23.7, 14.4

1. Cell Culture

Human embryonic kidney 293 (HEK293) cells were purchased from ATCC and cultured in a DMEM medium comprising 10% FBS at 37° C. and in 5% $CO_2$. To overexpress a ghrelin receptor, HEK293 cells were infected with a human ghrelin receptor cDNA vector (hGHSRa-pcDNA3.1+, cDNA Resource Center) and cultured for 48 hours. Thereafter, each triazole compound synthesized in the cell line and ghrelin were treated to evaluate efficacy as a ghrelin receptor agonist in terms of intracellular calcium influx, ghrelin receptor sub-signal factors and ghrelin receptor intracellular influx.

2. Intracellular Calcium Influx Experiment

HEK293 cells overexpressing a ghrelin receptor were treated with Fluo-2AM, a calcium-specific fluorescent factor, and, 1 hour later, washed twice with a wash buffer comprising 20 mM Hepes, 1 mM $CaCl_2$, 1 mM $MgCl_2$ and 0.7 mg/mL probenicid. After treating the cells with 100 ul of a wash buffer, fluorescently labeled intracellular calcium was imaged at an excitation wavelength of 485 nM and an emission wavelength of 520 nM for 1 minute at a shutter interval of 10 seconds under a laser scanning confocal microscope equipped with a temperature and humidity control equipment. Thereafter, ghrelin and triazole compounds were added for each concentration and then imaged under the same conditions. Intracellular calcium fluorescence intensity by treatment with compounds was quantified by calculating same based on the fluorescence intensity when not treated with compounds.

3. Immunofluorescence

HEK293 cells overexpressing a ghrelin receptor were treated with 10 mM each of ghrelin and a triazole compound, and, 1 hour later, the cells were fixed and cultured together with an anti-ghrelin receptor (rabbit, 1:500, abcam) for the ghrelin receptor. One day later, the cells were washed and cultured together with an anti-rabbit 488 antibody for 1 hour, and analyzed by using a laser scanning confocal microscope equipped with Fluoview SV1000 imaging software (Olympus FV1000, Japan). Metamorph software (Molecular Devices) was used to quantify the percentage of the area of the stained area of the ghrelin receptor introduced into the cells.

4. Western Blot

Protein expressions of pAMPK, AMPK, pPI3K, PI3K, pERK, and ERK were analyzed by using Western blotting. Antibodies to pAMPK, AMPK, pPI3K, PI3K, pERK, ERK (cell signaling) and β-actin (Santa Cruz) were used, and densitometric quantification was performed by using ImageJ software (US National Institutes of Health).

5. Analysis of a G Protein Coupled Receptor Agonist and Antagonist

The efficacy of triazole compounds (10 mM) as agonists and antagonists for a total of 170 types of G protein-coupled receptors was performed by Eurofins Discovery.

6. Establishment of Postoperative Ileus Mouse Model

Mice aged 6-8 weeks were fasted for one day and then anesthetized with a mixture of ketamine and xylazine. The abdomen and peritoneum were then incised, and the small intestine was exposed on a sterile gauze pad. Manipulation was performed from the duodenum to the cecum for 5 minutes by using a sterile cotton swab. After surgery, the abdomen was sutured and the mice were allowed to recover for 4 hours in a cage maintained at 32 degrees.

7. Evaluation of Delayed Gastric Emptying

Triazole compounds (10 mg/kg, 20 mg/kg and 30 mg/kg) were orally administered 20 hours after POI surgery. After 4 hours, 1.5% methylcellulose aqueous solution and 0.05% phenol red (Sigma) were orally administered. After 30 minutes, the stomach of the mouse was removed and put into a 0.1N NaOH 2 ml solution to homogenize same. 3 ml of 0.1N NaOH solution was added and centrifuged at 3000 rpm at 4 degrees for 10 minutes. After adding 100 ml of 20% trichloroacetic acid to the supernatant, the mixture was centrifuged at 3000 rpm at 4 degrees for 10 minutes. After adding 400 ml of 0.5N NaOH solution to 500 ml of the supernatant, absorbance was measured at 562 nm. For baseline control, the stomach was removed immediately after oral administration of 1.5% methylcellulose aqueous solution and 0.05% phenol red, and the absorbance was measured in the sample obtained through the above-identified process. The percentage of the gastric emptying delay was calculated by (1−(absorbance of test sample)/(baseline control absorbance)×100.

8. Evaluation of Colon Transit Time

To evaluate the colon transit time of feces, 200 ul of trypan blue dye was injected into the proximal colon before suturing after POI surgery. A triazole compound (30 mg/kg) was orally administered 4 hours after POI surgery. The mouse was transferred to a metabolic cage, and the weighed feed was administered thereinto, and the time at which the first feces stained with trypan blue appeared was measured for 24 hours. At the 24th hour, the number and weight of feces were measured, and the weight of the consumed feed and the mouse's body weight were measured.

9. Establishment of a Cancer Cachexia Model

To establish a cancer acinar model, CT26 (colon tumor 26 cell line) cells were purchased from ATCC (CRL-2638) and cultured in a RPMI1640 medium comprising 10% FBS at 37° C. and in 5% $CO_2$. Cultured $1\times10^6$ cells were subcutaneously injected into the right side of the abdomen of 10-week-old mice. The size of the cancer grown in the right abdomen, body weight, and feed intake were measured once every time after cell injection, and 10 mg/kg of a triazole compound was orally administered daily from the 9th day. On the 18th day of cancer cell injection, each of the grip test and Rota-rod test for evaluating the muscle function was performed for 1 day. On the 20th day, subcutaneous fat, visceral fat and muscle (femur, calf) of the mouse were separated and weighed.

10. Grip Test and Rota-Rod Test for Evaluating Muscle Function

For the evaluation of muscle function, the grip test was performed by holding the mouse by having the mouse hold the metal grid attached to the grip strength meter, holding the tail of the mouse, and pulling it from behind horizontally. The force applied to the metal grid immediately before losing the grip was recorded in the measuring instrument as the maximum tension in g, and the entire process was performed 9 times per subject to record the average value. In the Rota-rod test (Ugo Basile, Comerio, VA, Italy), Rota-rod exercise was performed at least three times at a rotational speed of 4 rpm by using a machine equipped with a rod with the diameter of 3 cm appropriately processed to provide grip to measure the endurance time of the tested animals in seconds and record the average value. Each Rota-rod behavior test was not to exceed 5 minutes per time.

11. Statistical Analysis

The repeated measures analysis of Tukey's HSD test and variance test were performed according to the SAS statistical package (release 9.1; SAS Institute Inc., Cary, NC) for comparison of multiple groups. *$p<0.05$, $p<0.01$, *$p<0.001$, and ****$p<0.0001$ were considered significant.

<Results of Experiment>

1. Confirmation of Effects as a Ghrelin Receptor Agonist from Increase of Intracellular Calcium Influx In order to confirm the efficacy of triazole compounds as ghrelin receptor agonists, changes in intracellular calcium influx, which is a major function of ghrelin, were first measured. HEK293 cells overexpressing a human ghrelin receptor were reacted with a calcium-labeled fluorescent factor for 1 hour and then treated with ghrelin and triazole compounds KARI001, KARI101, and KARI201 for each concentration. As a result, it was confirmed that intracellular calcium influx increased as the concentration of the three triazole compounds increased (see FIG. 1). The EC50, which is the concentration capable of inducing 50% intracellular calcium influx, was confirmed to have ghrelin=39.45 nM, KARI001=128.3 nM, KARI101=188.5 nM, and KARI201=272.9 nM.

That is, it was confirmed that the three triazole compounds could induce intracellular calcium influx as ghrelin receptor agonists.

2. Effect as a Ghrelin Receptor Agonist Through the Regulation of G Protein-Dependent Subfactors of a Ghrelin Receptor It is known in the art that a ghrelin receptor is a G protein-coupled receptor, and, when ghrelin binds to the ghrelin receptor, the activities of different sub-signal factors are regulated depending on three major types of G proteins. For example, Gaq-dependent signaling increases intracellular calcium influx to increase AMPK factor phosphorylation, and Gai/o-dependent signaling increases PI3K factor phosphorylation. B-arrestin-dependent signaling increases ERK factor phosphorylation or induces ghrelin receptor intracellular influx (FASEB J. 2019; 33(1):518-531).

Figure 2:
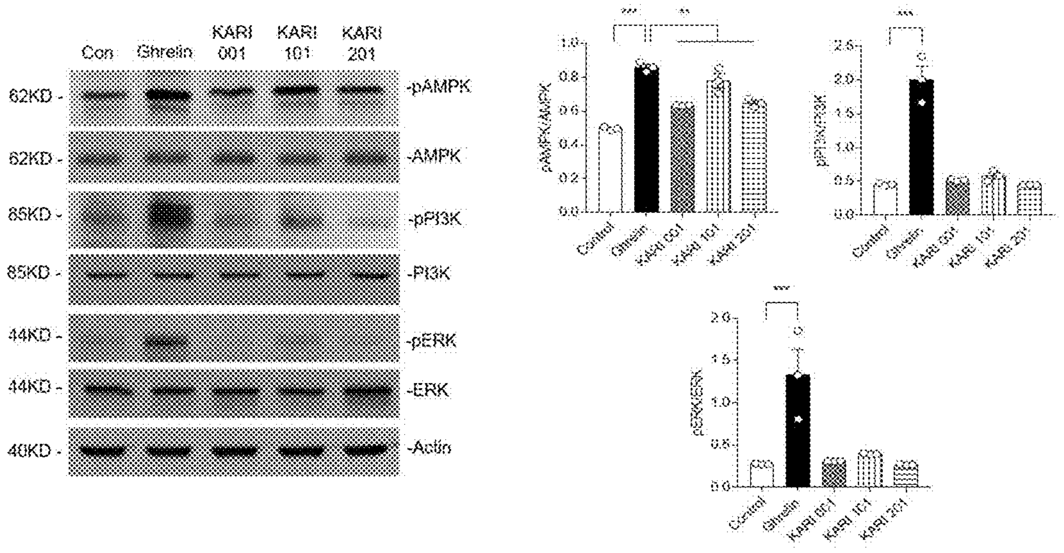
FIG. 2 is a diagram showing changes in ghrelin receptor subsignal factors by treatment with 10 mM of ghrelin and triazole compounds (KARI001, KARI101 and KARI201) in HEK293 cells overexpressing a ghrelin receptor (n=3, $^{}p<0.01$, $^{*}p<0.001$).

First, it was checked whether or not the three triazole compounds could regulate the phosphorylation of G protein-dependent signaling subfactors of the ghrelin receptor. HEK293 cells overexpressing a human ghrelin receptor were treated with 10 mM of ghrelin and three triazole compounds, cell proteins were extracted 1 hour later, and it was checked whether or not sub-factors were phosphorylated by using Western blotting. As a result, it was observed that the three triazole compounds could increase phosphorylation of AMPK factors (see FIG. 2).

Figure 3:
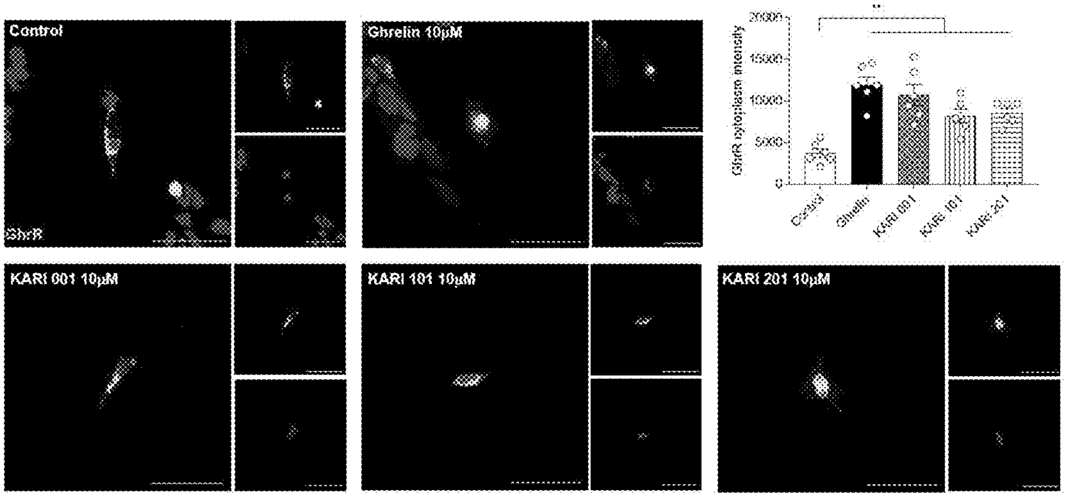
FIG. 3 is a diagram showing the intracellular influx efficacy of a ghrelin receptor by treatment with 10 mM of ghrelin and triazole compounds (KARI001, KARI101 and KARI201) in HEK293 cells overexpressing a ghrelin receptor (n=6, $^{**}p<0.01$).

In addition, in order to confirm the effect of the ghrelin receptor intracellular influx, HEK293 cells overexpressing a human ghrelin receptor were treated with 10 mM ghrelin and three triazole compounds, a ghrelin receptor antibody was cultured 1 hour later, and it was checked whether or not an intracellular ghrelin receptor was expressed. As a result, it was observed that cells not treated with ghrelin and three triazoles expressed ghrelin receptors in the cell membrane, whereas cells treated with ghrelin and three types of triazoles expressed ghrelin receptors in the perinuclear cytoplasm (see FIG. 3).

That is, it was found that the three triazole compounds were effective as agonists capable of regulating Gaq-dependent signaling and B-arrestin-dependent signaling of ghrelin receptors.

3. Effect of Triazole Compounds as Ghrelin Receptor-Specific Agonists

Figure 4A:
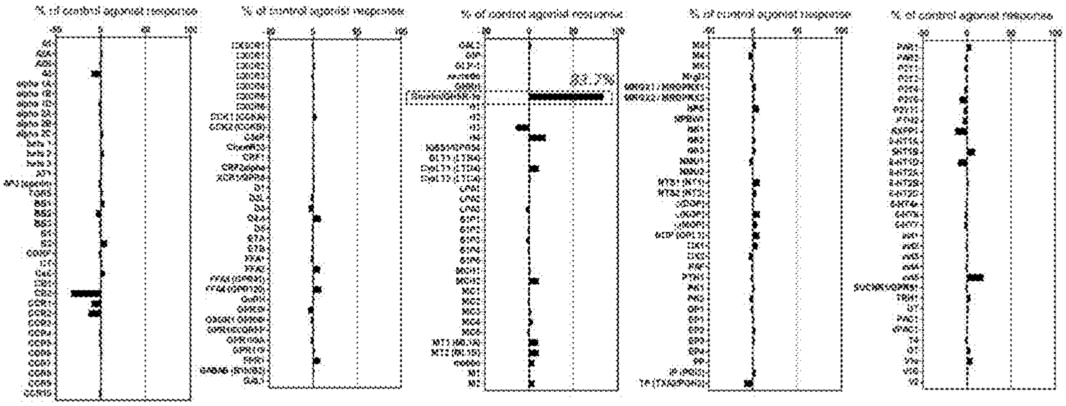
FIGS. 4A and 4B are diagrams showing the efficacy of a triazole compound (KARI201) as an agonist or antagonist for 170 G-protein coupled receptors comprising a ghrelin receptor.
Figure 4B:
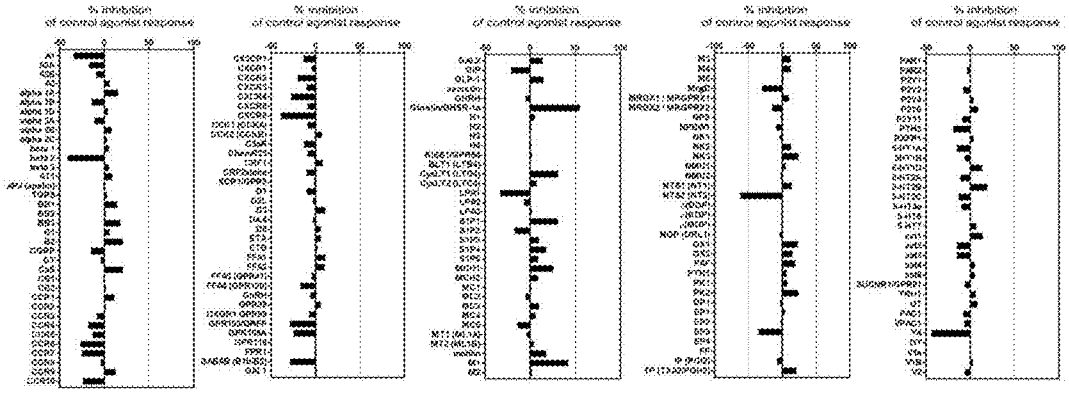
Figure 5A:
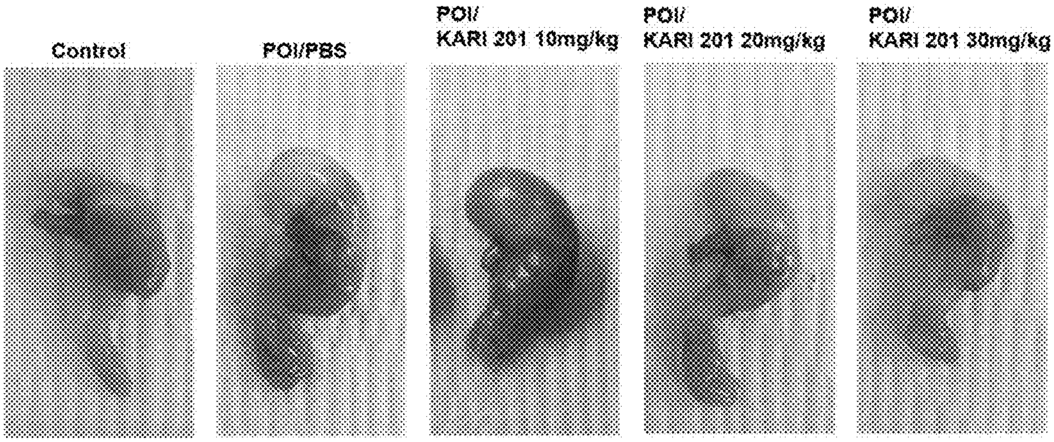
FIGS. 5A and 5B are diagrams showing the effect of improving delayed gastric emptying, which may evaluate the motor function of the stomach of a postoperative ileus (POI) mouse model after oral administration of a triazole compound (KARI 201) at different concentrations (n=5-10, $^{*}p<0.05$, $^{**}p<0.01$).
Figure 5B:
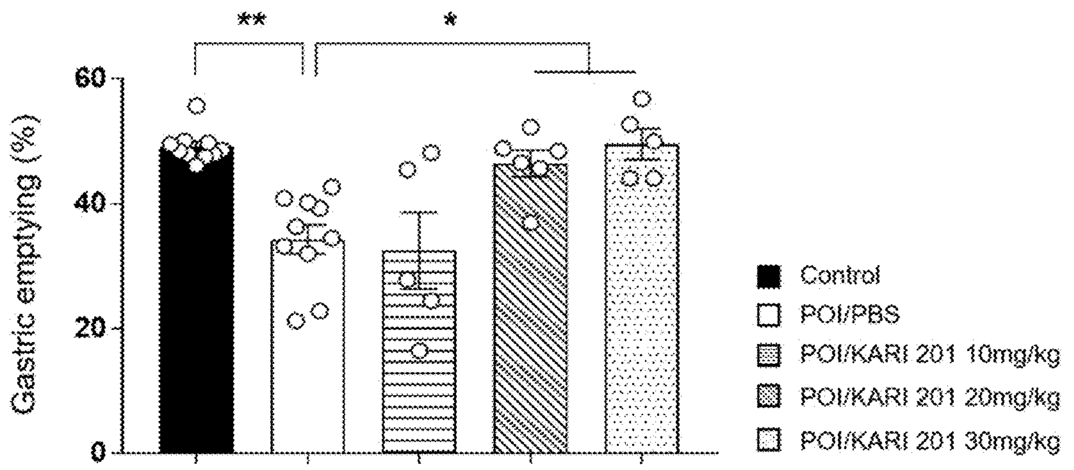
Figure 6A:
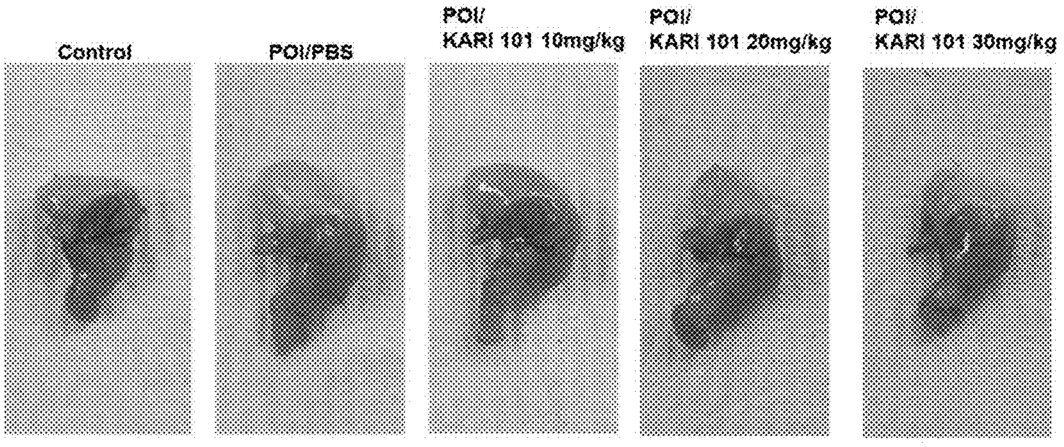
FIGS. 6A and 6B are diagrams showing the effect of improving delayed gastric emptying, which may evaluate the motor function of the stomach of a postoperative ileus (POI) mouse model after oral administration of a triazole compound (KARI 101) at different concentrations (n=5, $^{}p<0.01$, $^{*}p<0.001$).
Figure 6B:
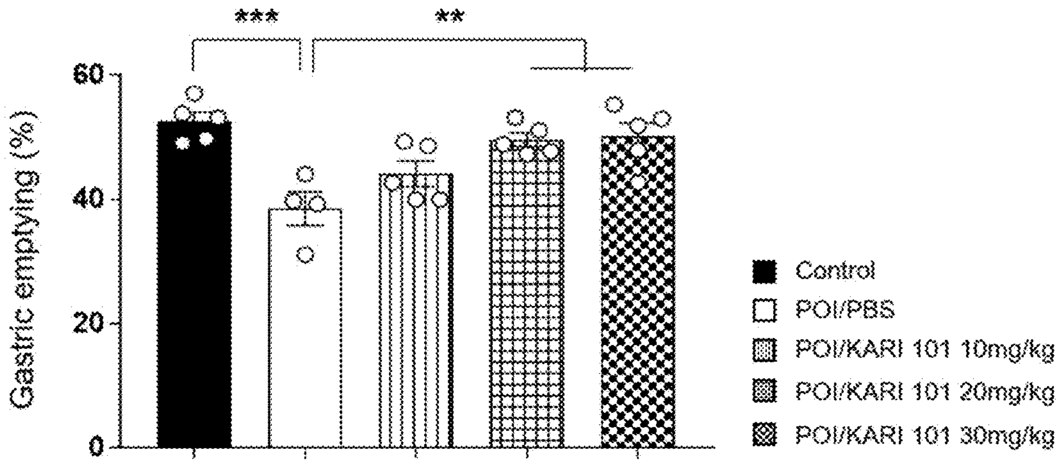

The family of G protein-coupled receptors comprises many types of receptors comprising a ghrelin receptor. It was checked whether or not the triazole compounds have efficacy as agonists or antagonists of different types of G protein-coupled receptors. Different cell lines expressing a total of 170 G protein-coupled receptors comprising the ghrelin receptor were treated with 10 mM of triazole compound KARI201 alone (agonist effect) or together with ligands for each receptor (antagonist effect). As a result, it was confirmed that KARI201 only exhibited 83.7% efficacy as a ghrelin receptor agonist (see FIGS. 4A and 4B).

That is, through this result, it was found that the KARI201 triazole compound was effective as a ghrelin receptor-specific agonist.

4. Effect of Triazole Compounds of Improving Delayed Gastric Emptying

In order to confirm the gastric motility promoting effect, which is one of the representative physiological effects of ghrelin as a ghrelin receptor, postoperative intestinal obstruction (POI) mice were used. POI mice whose intestinal obstruction was induced showed a delayed gastric emptying effect compared to normal mice, while POI mice administered with KARI201 and KARI101 20 hours after POI surgery showed a significant improvement in delayed gastric emptying as the concentration increased (see FIGS. 5A, 5B, 6A and 6B).

That is, it was found that triazole compounds KARI201 and KARI101 are ghrelin receptor agonists and are effective in improving delayed gastric emptying by improving the gastric motor function.

5. Improvement of Triazole Compounds of Colon Motor Function

Figure 7A:
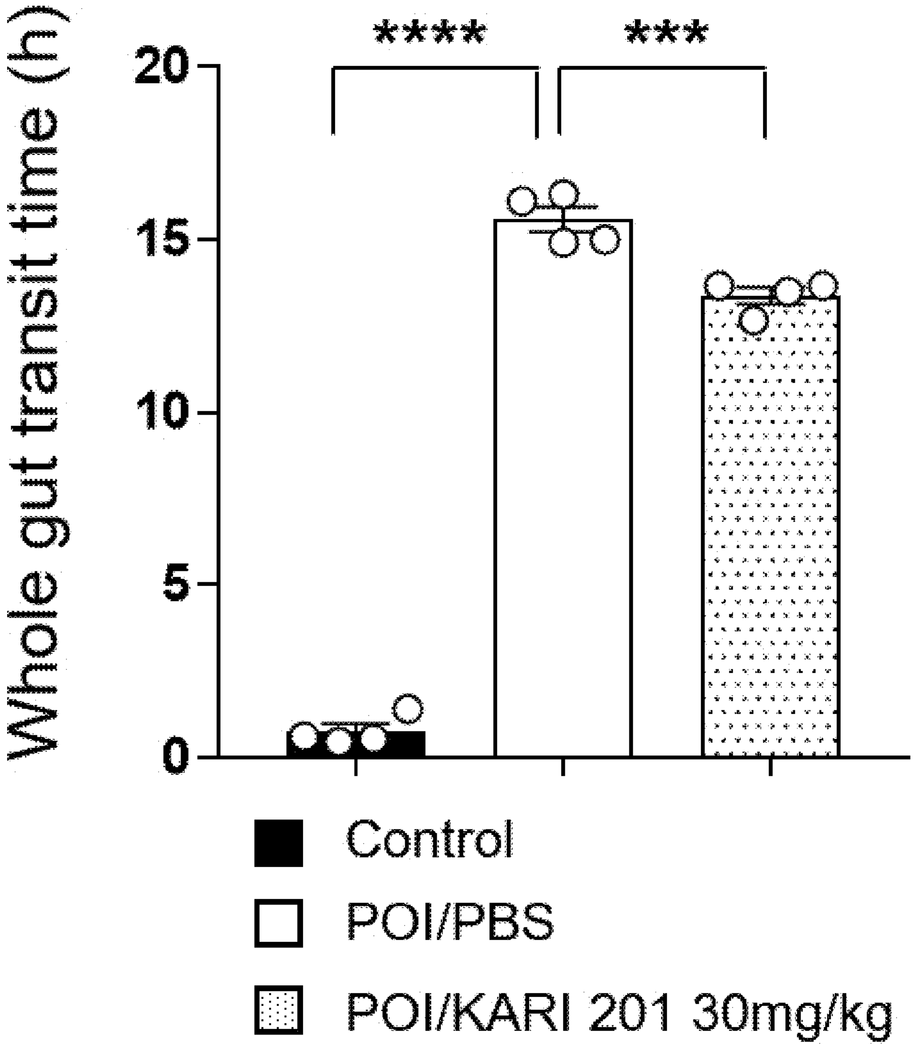
FIGS. 7A to 7D are diagrams showing the colon transit time of feces (FIG. 7A), number and weight of feces (FIG. 7B), feed intake (FIG. 7C) and body weight (FIG. 7D), which may evaluate the motor function of the colon of a postoperative ileus (POI) mouse model after oral administration of 30 mg/kg of a triazole compound (KARI 201) (n=4, $^{*}p<0.001$, $^{**}p<0.0001$).
Figure 7B:
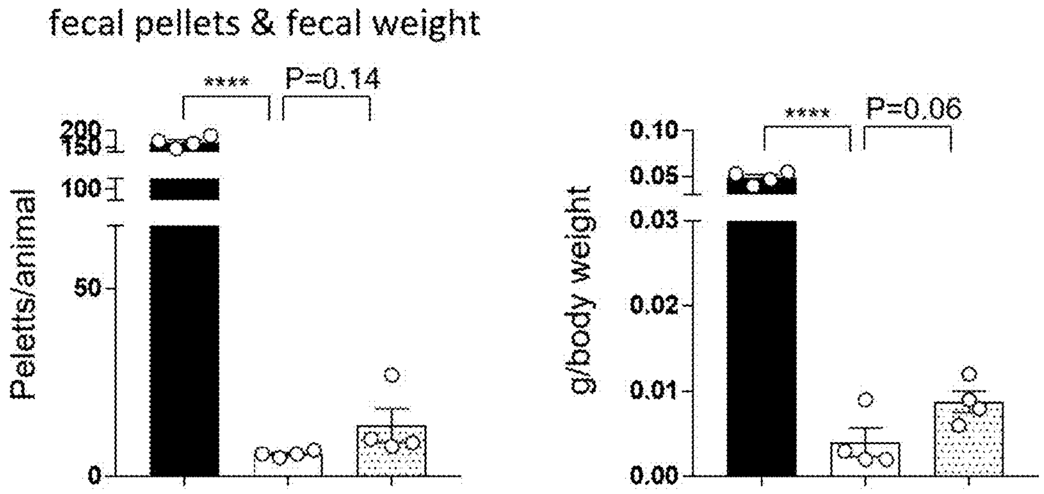
Figure 7C:
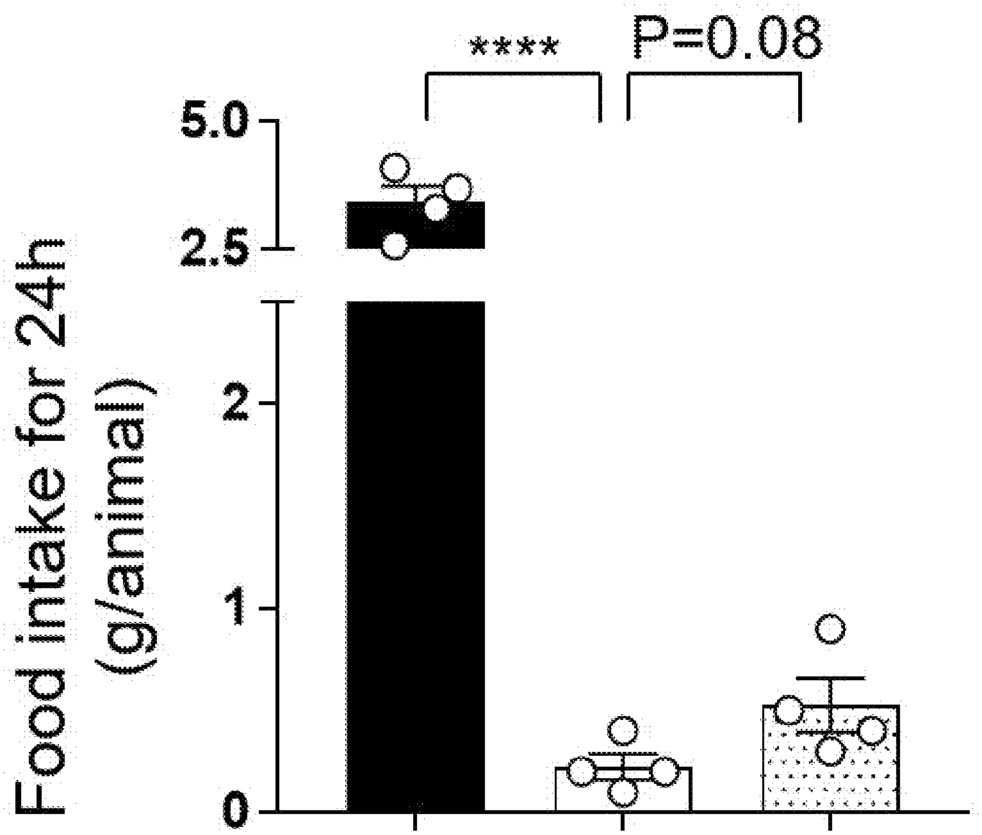
Figure 7D:
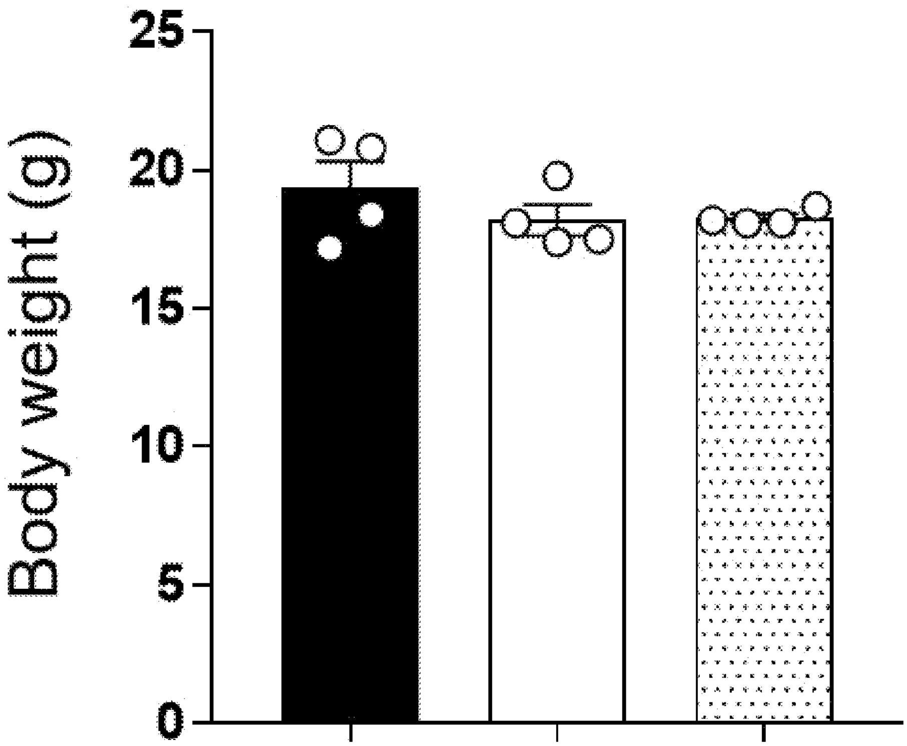
Figure 8A:
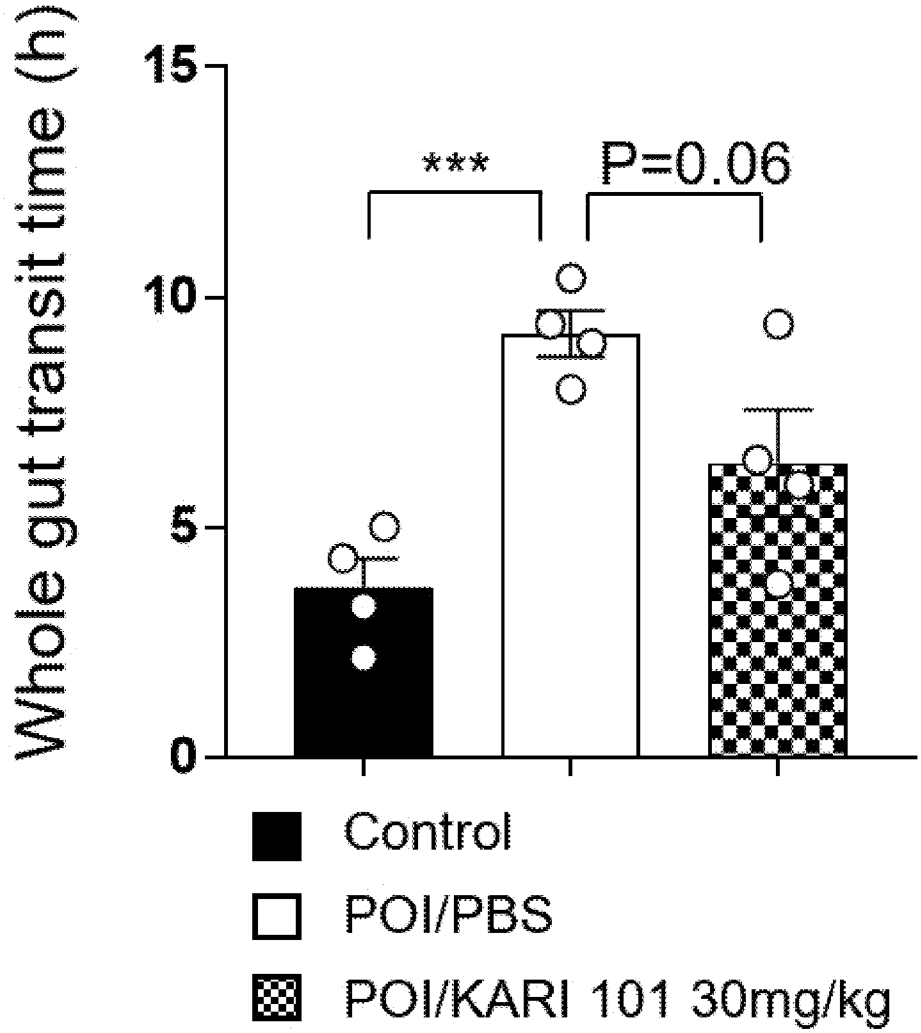
FIGS. 8A to 8D are diagrams showing the colon transit time of feces (FIG. 8A), number and weight of feces (FIG. 8B), feed intake (FIG. 8C) and body weight (FIG. 8D), which may evaluate the motor function of the colon of a postoperative ileus (POI) mouse model after oral administration of 30 mg/kg of a triazole compound (KARI 101) (n=4, $^{*}p<0.05$, $^{}p<0.01$, $^{*}p<0.001$).
Figure 8B:
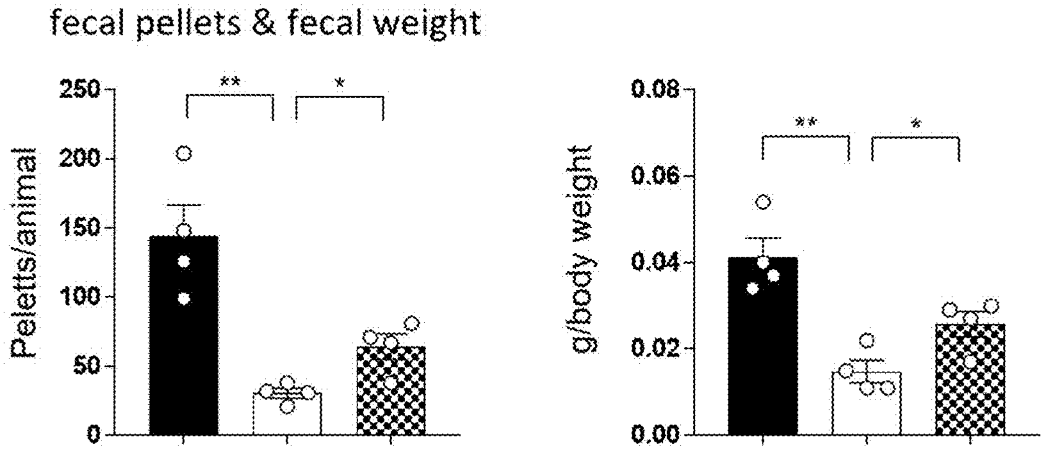
Figure 8C:
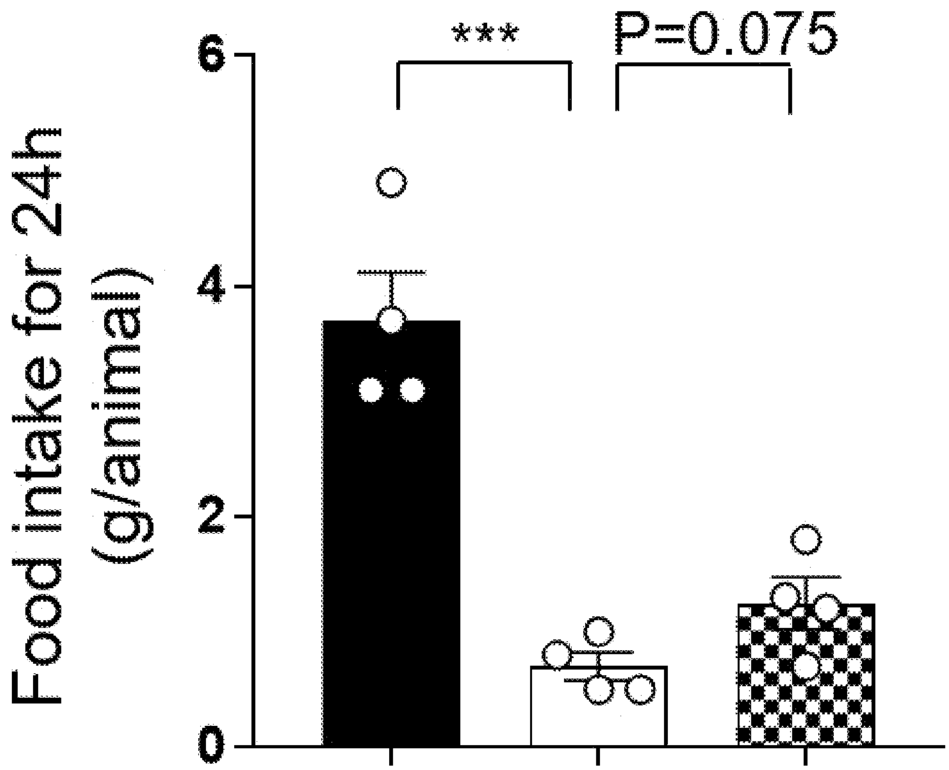
Figure 8D:
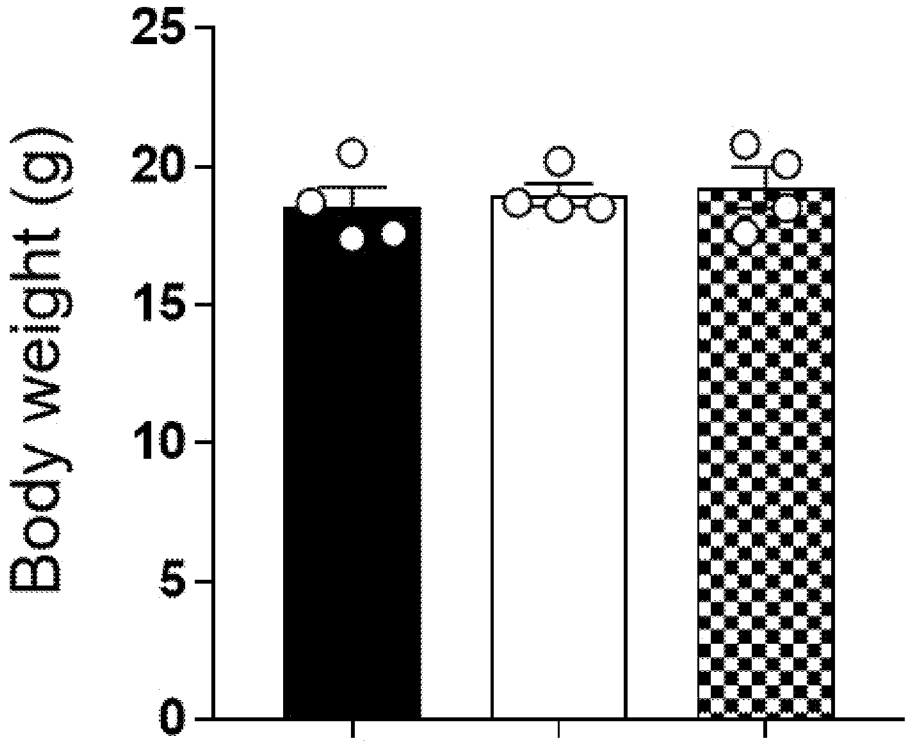

Based on the effect of triazole compounds KARI201 and KARI101 of delaying gastric emptying, it was checked whether or not they could improve the colon transit time of feces in POI mice. The mice administered with PBS 4 hours after POI surgery showed a long colon transit time of feces, whereas the mice administered with 30 mg/kg of KARI201 or KARI101 showed a significantly reduced colon transit time of feces (see FIGS. 7A and 8A). The number and weight of feces also increased by the administration of KARI201 (see FIGS. 7B and 8B). Feed intake also increased as compared to that of POI mice administered with PBS, whereas there was no change in their body weights (see FIGS. 7C, 7D, 8C and 8D).

That is, it was found that triazole compounds KARI201 and KARI101 as ghrelin receptor agonists also improve colon motor function and thus are effective for improving the excretion time of feces. Therefore, it was found that the triazole compounds may be very useful as preventives or therapeutic agents for diseases mediated by a ghrelin receptor.

6. Effect of Triazole Compounds of Improving Strength and Function

Figure 9A:
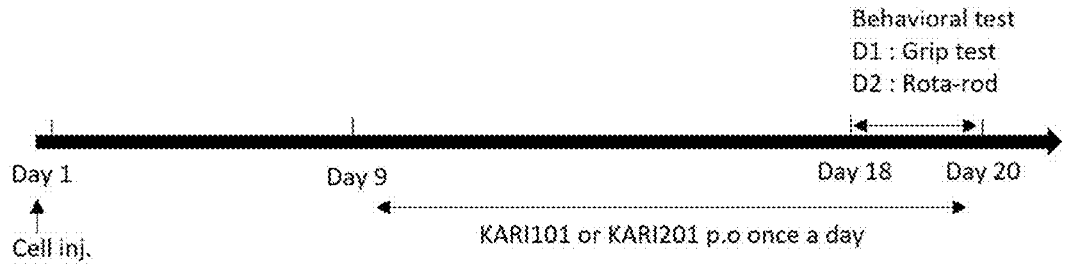
FIGS. 9A to 9C are diagrams confirming the outline of experiments performed to investigate the efficacy of triazole compounds (KARI 101 and KARI 201) in a cancer cachexia mouse model (FIG. 9A) and the effect of improving muscle strength and function after oral administration of 10 mg/kg of such compounds (FIG. 9B) (n=7-8, $^{*}p<0.05$, $^{}p<0.01$, $^{*}p<0.001$).
Figure 9B:
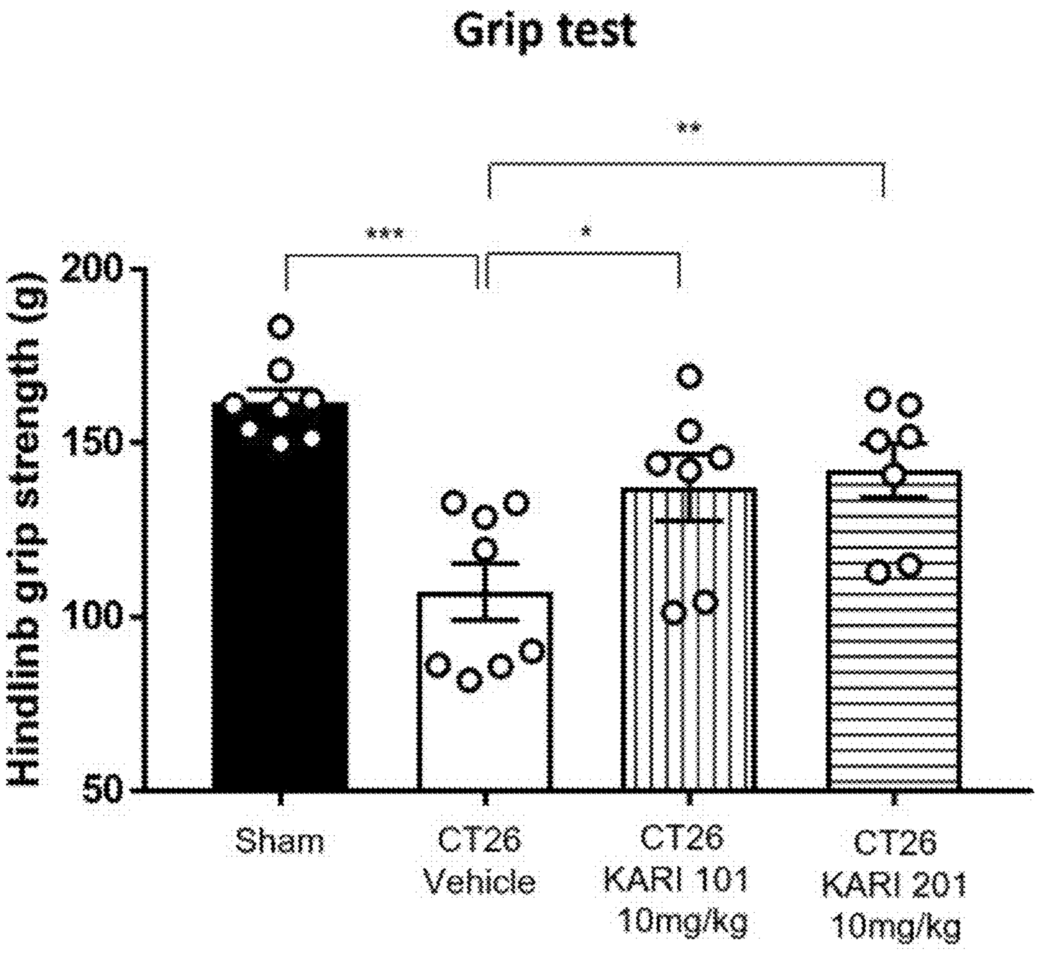
Figure 9C:
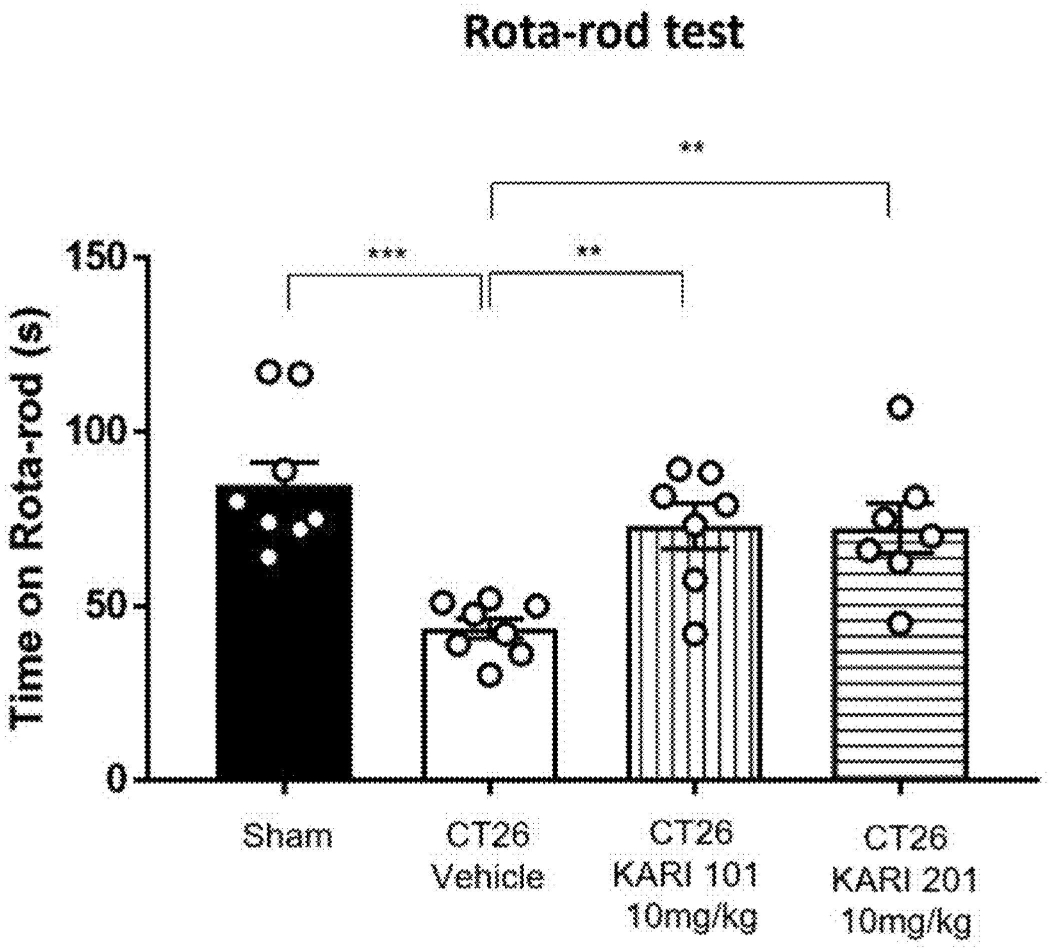

Cancer cachexia mice were used to confirm the increase in feed intake, which is another physiological effect of ghrelin as a ghrelin receptor, and consequent improvement in fat and muscle loss. To establish a cancer cachexia mouse model, CT26 cancer cells were subcutaneously injected into the right abdominal layer of 10-week-old mice. It was confirmed that cancer cells grew in the right abdomen on the 9th day after cell injection, and 10 mg/kg of KARI101 and KARI201 were orally administered once daily. On the 18th day, Grip test and Rota-rod test were performed to evaluate muscle strength function (see FIG. 9A). It was confirmed that muscle strength function decreased in cancer cachectic mice injected with Vehicle, whereas muscle strength function was significantly improved in cancer cachexic mice administered with KARI101 or KARI201 (see FIGS. 9B and 9C).

7. Effect of Triazole Compound of Improving Feed Intake and Fat and Muscle Loss

Figure 10A:
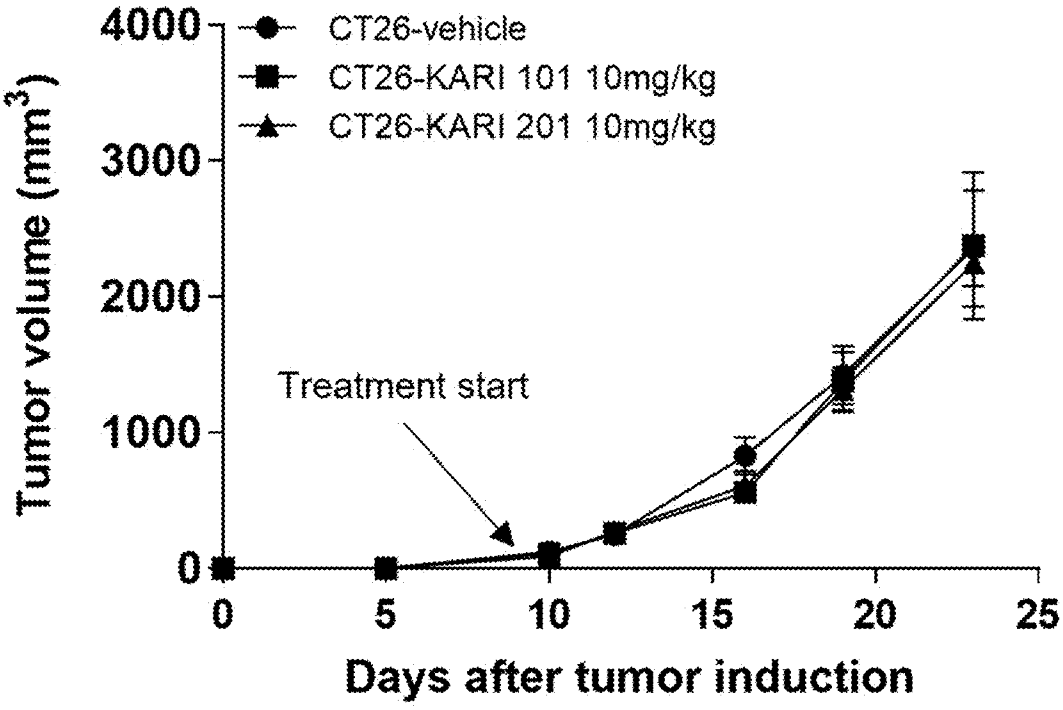
FIGS. 10A to 10D are diagrams showing the cancer size (FIG. 10A), body weight (FIG. 10B), feed intake (FIG. 100) and average daily feed intake (FIG. 10D) of a cancer cachexia mouse model for the duration of oral administration of 10 mg/kg of triazole compounds (KARI 101 and KARI 201) (n=9, $^{}p<0.01$, $^{**}p<0.0001$).
Figure 10B:
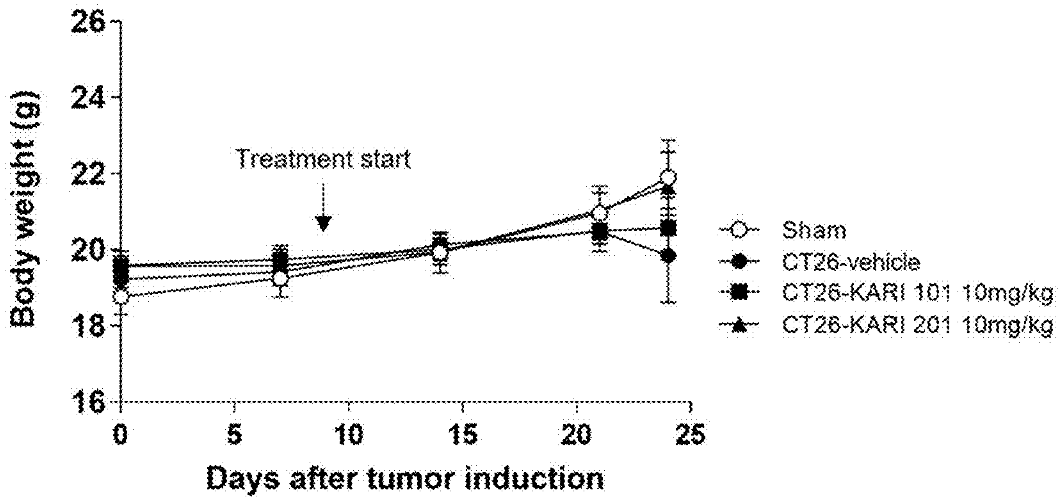
Figure 10C:
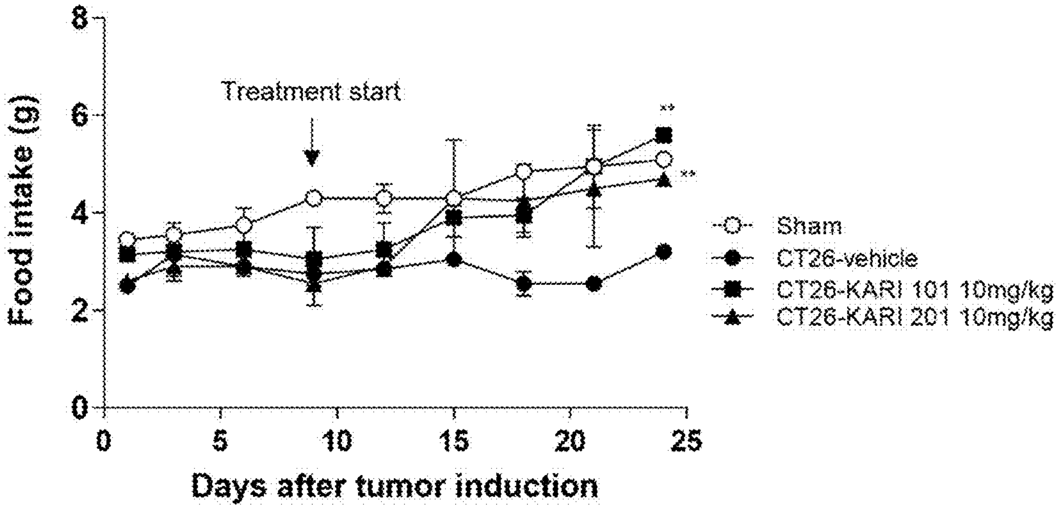
Figure 10D:
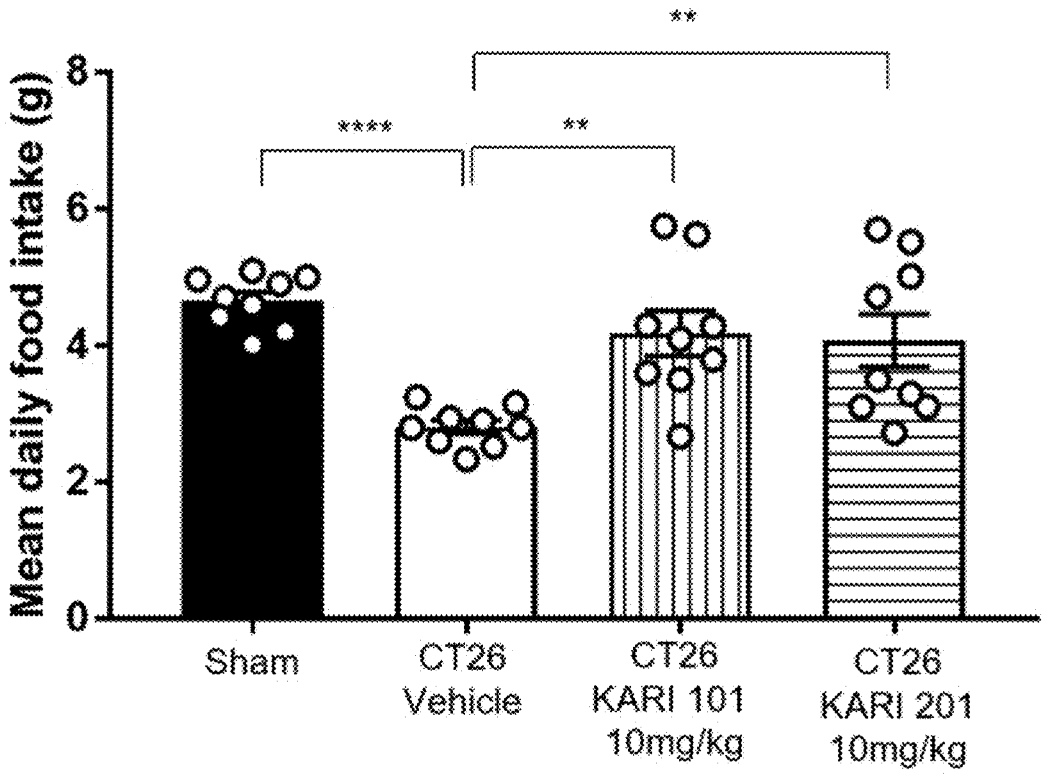
Figure 11A:
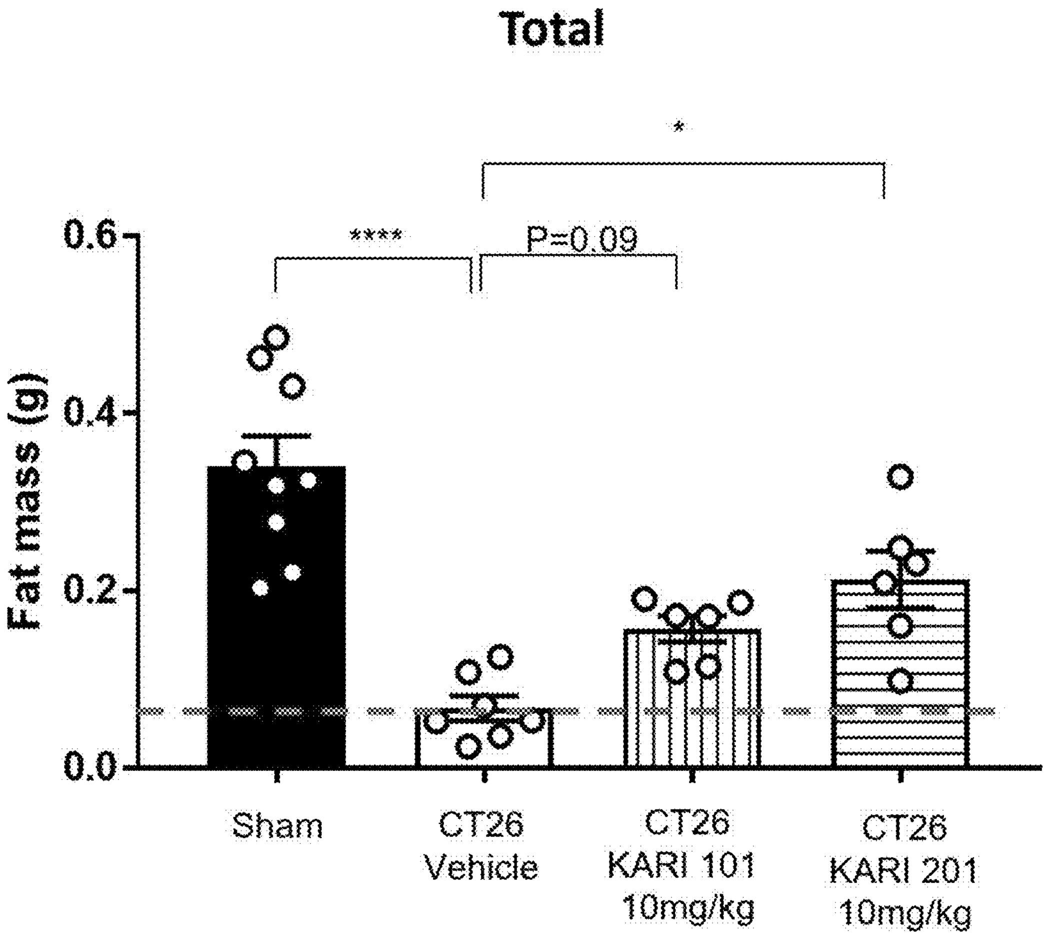
FIGS. 11A to 11D are diagrams showing the total fat weight (FIG. 11A), visceral fat weight (FIG. 11B), subcutaneous fat weight (FIG. 11C) and muscle weight (FIG. 11D) of a cancer cachexia mouse model after oral administration of 10 mg/kg of triazole compounds (KARI 101, KARI 201) (n=6-9, $^{*}p<0.05$, $^{}p<0.01$, $^{**}p<0.0001$).
Figure 11B:
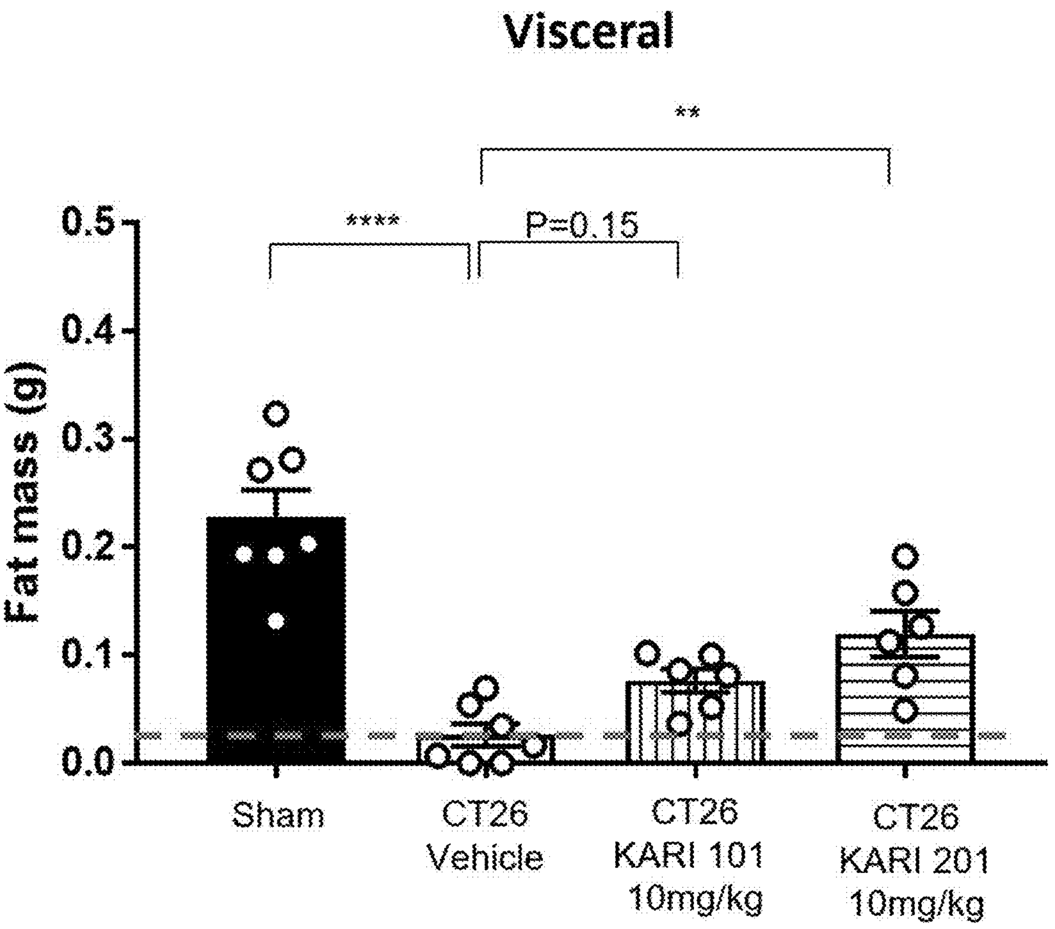
Figure 11C:
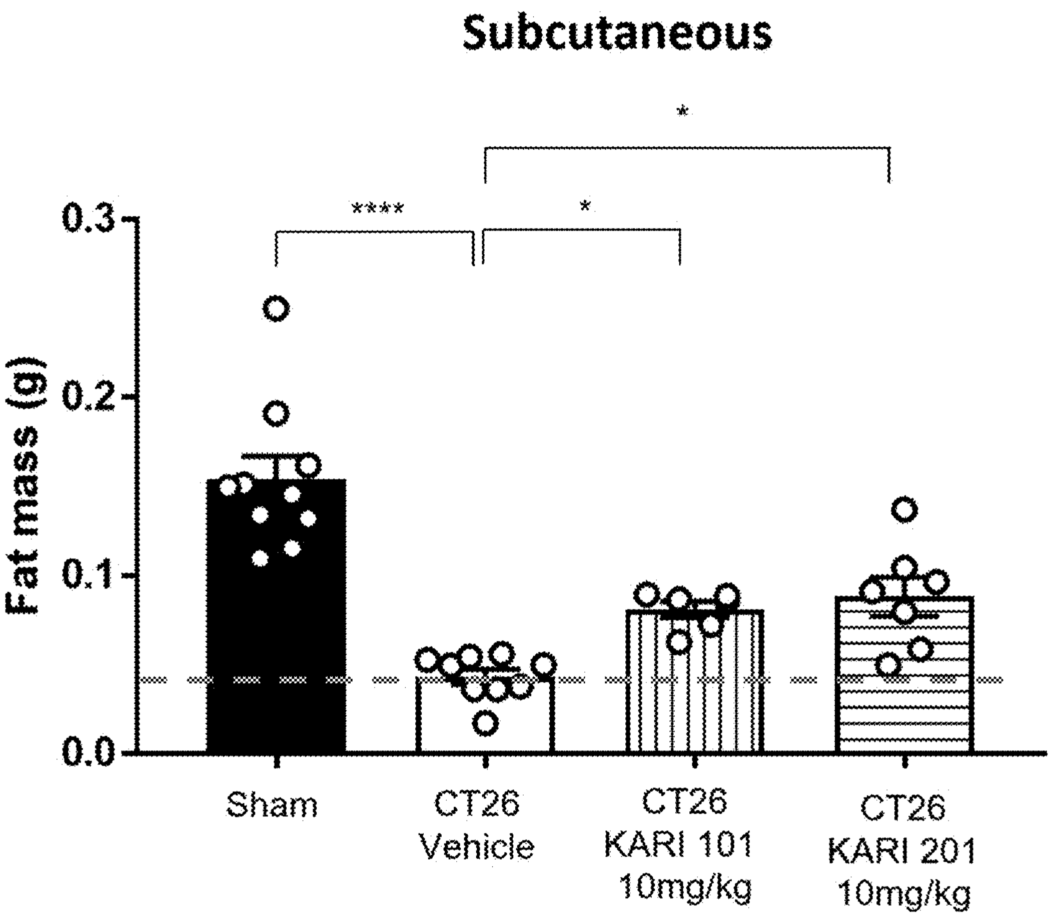
Figure 11D:
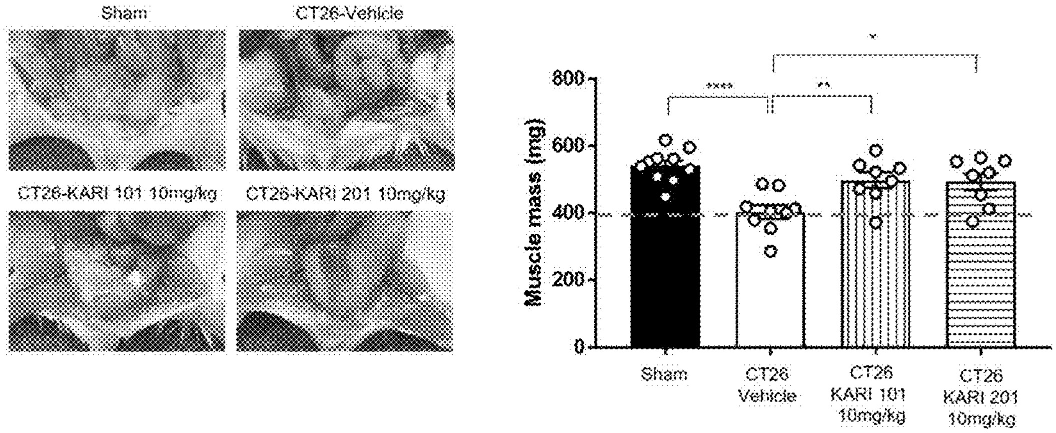

Based on the effect of triazole compounds KARI101 and KARI201 of improving muscle strength and function in a cancer cachexia mouse model, cancer size, body weight and feed intake were evaluated. Administration of KARI101 and KARI201 did not affect the cancer size (see FIG. 10A) and body weight (see FIG. 10B) of cancer cachexia mice, but increased daily feed intake as compared to cancer cachexia mice administered with Vehicle (see FIGS. 100 and 10D). In addition, KARI101 and KARI201 administration increased reduced total fat (FIG. 11A), visceral (see FIG. 11B) and subcutaneous fat (FIG. 11C) and increased reduced muscle mass (see FIG. 11D), as compared to cancer cachexia mice administered with Vehicle.

That is, it was found that triazole compounds KARI201 and KARI101 as ghrelin receptor agonists can increase the reduced feed intake of cancer cachectic mice and, thus, are effective for improving the reduced fat and muscle mass and muscle strength function.

INDUSTRIAL APPLICABILITY

The compound provided by the present invention exhibits a very strong binding force with very high specificity to a ghrelin receptor and thus is very useful for preventing or developing a preventive or therapeutic agent for diseases mediated by a ghrelin receptor and has high industrial applicability.

The invention claimed is:

1. A method for treating diseases mediated by a ghrelin receptor, wherein the diseases mediated by the ghrelin receptor are selected from the group consisting of eating disorders; cancer anorexia or cachexia; cachexia or anorexia due to anticancer drugs; hyperalgesia due to anticancer drugs; chronic obstructive pulmonary disease (COPD) or COPD cachexia; sarcopenia; weight loss; generalized weakness after surgery in cancer patients; chronic airway infection; inflammation; inflammatory bowel disease (IBD); functional dyspepsia (FD); constipation; diabetic gastroparesis; heart failure; myocardial infarction; diabetic neuropathy; growth hormone deficiency; defecation disorders in patients with spinal injuries; postoperative ileus; anoxia; and morphine-induced intestinal obstruction, comprising administering an effective amount of a composition comprising a compound of the following Formula 1 or a pharmaceutically acceptable salt thereof to a subject in need thereof:

[Formula 1]

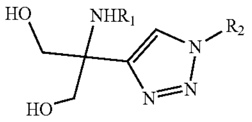

wherein $R_1$ is hydrogen; straight or branched chain alkyl having 1 to 15 carbon atoms; or substituted or unsubstituted alkylcarbonyl having 1 to 5 carbon atoms, and R2 is hydrogen; straight or branched chain alkyl having 1 to 15 carbon atoms; alkenyl having 2 to 10 carbon atoms; or alkynyl having 2 to 10 carbon atoms.

2. The method of claim 1, wherein $R_1$ is hydrogen.

3. The method of claim 1, wherein $R_2$ is straight-chain or branched-chain alkyl having 1 to 15 carbon atoms.

* * * * *